(12) United States Patent
Zheng

(10) Patent No.: US 9,969,753 B2
(45) Date of Patent: May 15, 2018

(54) BCR-ABL DIPLOID INHIBITOR, SYNTHESIZING METHOD THEREFOR, AND USES THEREOF

(71) Applicant: CHENGDU UNIVERSITY, Chengdu, Sichuan (CN)

(72) Inventor: Zhebin Zheng, Sichuan (CN)

(73) Assignee: SHENZHEN YONGZE PHARMACEUTICAL CO., LTD., Shenzhen (CN)

(*) Notice: Subject to any disclaimer, the term of this patent is extended or adjusted under 35 U.S.C. 154(b) by 0 days. days.

(21) Appl. No.: 15/304,438

(22) PCT Filed: Apr. 16, 2015

(86) PCT No.: PCT/CN2015/076804
§ 371 (c)(1),
(2) Date: Oct. 14, 2016

(87) PCT Pub. No.: WO2015/158291
PCT Pub. Date: Oct. 22, 2015

(65) Prior Publication Data
US 2017/0037061 A1  Feb. 9, 2017

(30) Foreign Application Priority Data

Apr. 16, 2014 (CN) .......................... 2014 1 0151668
Apr. 17, 2014 (CN) .......................... 2014 1 0154836

(51) Int. Cl.
| | | |
|---|---|---|
| C07D 401/14 | (2006.01) |
| C07D 403/14 | (2006.01) |
| C07D 487/04 | (2006.01) |
| A61K 31/496 | (2006.01) |
| A61K 31/506 | (2006.01) |
| A61P 35/00 | (2006.01) |
| C07D 519/00 | (2006.01) |

(52) U.S. Cl.
CPC .......... *C07D 519/00* (2013.01); *A61K 31/496* (2013.01); *A61K 31/506* (2013.01); *C07D 401/14* (2013.01); *C07D 403/14* (2013.01); *C07D 487/04* (2013.01)

(58) Field of Classification Search
CPC .. C07D 401/14; C07D 403/14; C07D 484/04; A61K 31/496; A61K 31/506
USPC ............... 544/295, 296, 357; 514/252.1, 256
See application file for complete search history.

(56) References Cited

FOREIGN PATENT DOCUMENTS

| | | |
|---|---|---|
| WO | 2003037384 A2 | 5/2003 |
| WO | 2010120386 A1 | 10/2010 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Amy Card et al., "High-Throughput Biochemical Kinase Selectivity Assays: Panel Development and Screening Applications", Journal of Biomolarcular Screening, 14 (1) 2009.
Jude Dunne et al., "Comparison of On-Chip and Off-Chip Microfluidic Kinase Assay Formats", Assay & Drug Development Technologies vol. 2, No. 2, 2004.

* cited by examiner

*Primary Examiner* — Venkataraman Balasubramanian
(74) *Attorney, Agent, or Firm* — Novick, Kim & Lee, PLLC; Allen Xue

(57) ABSTRACT

Disclosed are compounds or pharmaceutically acceptable salts thereof having the following general formula: R-Linker-R. The compounds or pharmaceutically acceptable salts thereof provided by the present invention are used as Bcr-Abl diploid inhibitors, which can effectively inhibit the activity of tyrosine kinase, are applicable in treating diseases concerning abnormal activation of such kinases, and have good effects in treating malignant tumors. The method for preparing such inhibitors is simple and convenient, has low cost, and has good application prospects.

16 Claims, 1 Drawing Sheet

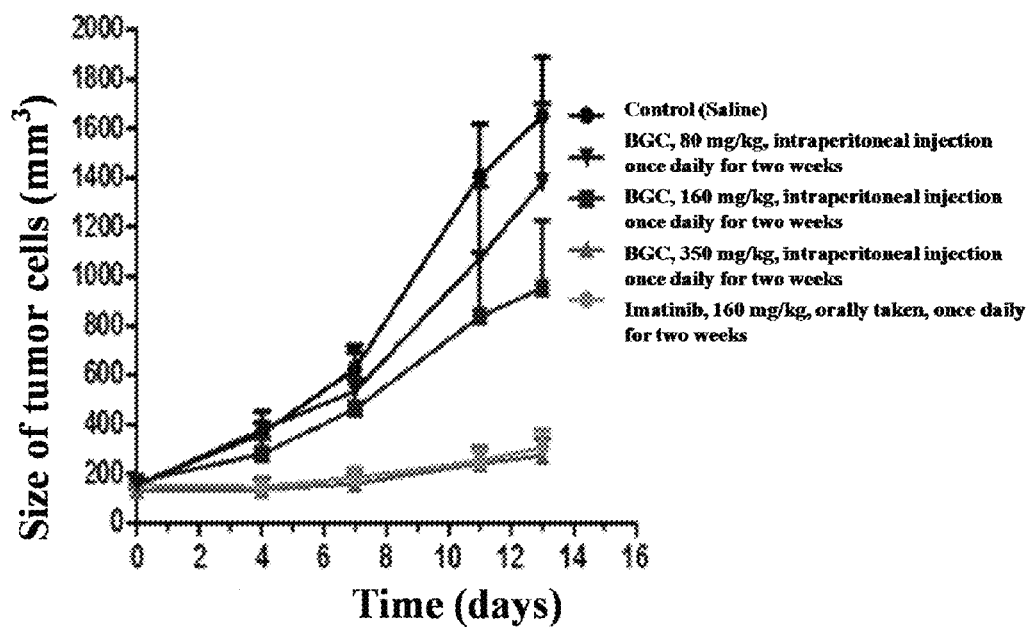

BCR-ABL DIPLOID INHIBITOR, SYNTHESIZING METHOD THEREFOR, AND USES THEREOF

FIELD OF THE INVENTION

The present invention relates to BCR-ABL diploid inhibitor, synthesizing method therefor, and uses thereof.

BACKGROUND OF THE INVENTION

Chronic myeloid leukemia is chromosome mutations [t(9: 22)(q34;q11)] reciprocal translocation, where BCR-ABL fusion by chromosome 9 ABL gene and chromosome 22 BCR gene, this gene encodes a 210 kDa tyrosine kinase BCR-ABL fusion, this protein is a major cause of chronic myelogenous leukemia. C-Abl in normal haploid cells are present in the cytoplasm in the tyrosine kinase, and Bcr fused form changes, which means change from haploid tetramers, which has always been the kinase activation, causes the tumors' occurrence. Bcr in protein sequences can cause polymerization of amino acid sequence which Bcr-Abl tetrapolymerized. Due to the c-Abl play an important role in myocardial cells, if carcinogenicity inhibitor Bcr-Abl selectively developed instead of Abl inhibitor, it is expected to significantly reduce such inhibitors' wide range of side effects, such as cardiac toxicity.

In 2001, FDA approved the first receptor tyrosine kinase inhibitor (TKI) Imatinib 1, for the treatment of chronic myelogenous leukemia (CML). As the first generation of Bcr-Abl inhibitors, Imatinib has become the first line drugs to treat CML. But most patients are resistant to Imatinib. Subsequent studies showed that IM drug resistance may be related to the Abl kinase activity of gene mutation such as G250E, Q252H, Y253F, Y253H, E255K, E355G, E255V, T315A, T315I, F317L, F317V, M351T, F359V, H396P, M244V. Genetic mutation leads to decreased affinity of Imatinib and Abl kinase. Most mutation decreased the affinity of Imatinib by 5-30 times. This is the main reason of drug resistance. T315I is special, and it reduced most obviously, $IC_{50}$ to 6400 nM. Recently developed Ponatinib is not only valid for the T315I, but also valid for the wild type and most mutants.

With the view of x-Ray eutectic structure of Imatinib and the Abl protein kinase, the n-methyl piperazine in the structure exposed to the solvent, the linear distance between the nitrogen atoms of the two inhibitors is about 24 au. Because of the tetramer structure of Bcr-Abl, it can be combined with 4 inhibitors. If the two inhibitors are connected with chain, it is expected to greatly enhance the affinity of Bcr-Abl, so as to play a role in selective inhibition of Bcr-Abl, while the Abl is haploid, only combined with one inhibitor, the diploid inhibitor has no impact to the affinity of the enzyme.

CONTENTS OF THE INVENTION

The object of the present invention is to provide BCR-ABL diploid inhibitor, synthesizing method therefor, and uses thereof.

The present invention provides compounds or pharmaceutically acceptable salts thereof have the following general formula: R-Linker-R, wherein R is 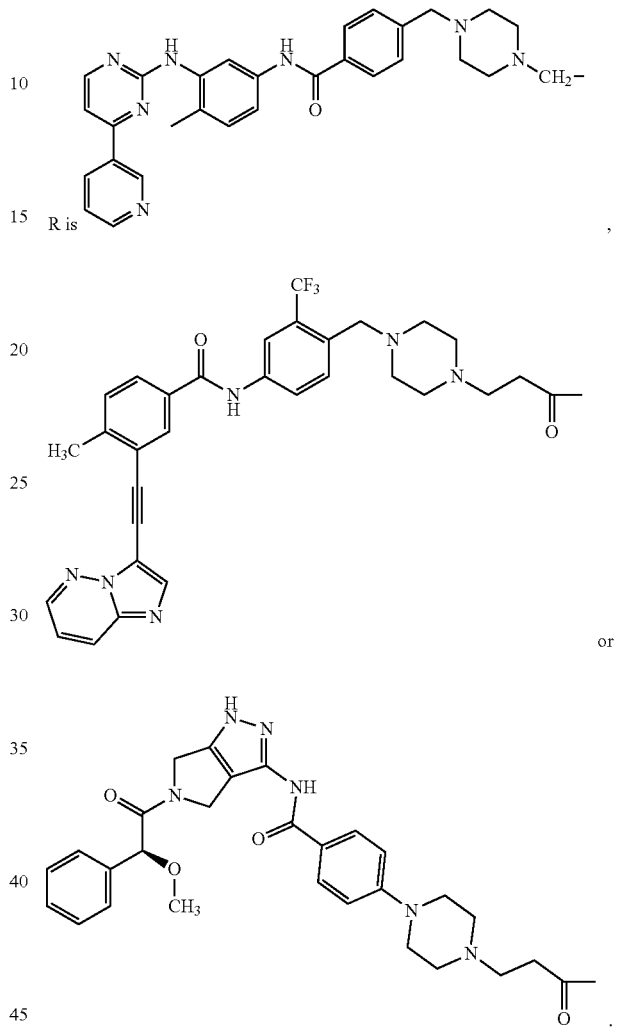, or The compounds or pharmaceutically acceptable salts thereof, wherein the linker is —$(CH_2CH_2O)_{x3}$—$(CH_2)_{x2}$—(NHCO)—$(CH_2)_{x1}$—(CONH)—$(CH_2)_{x2}$—$(OCH_2CH_2)_{x3}$—, in which, x1, x2 and x3 each independently represent 1, 2, 3, 4, 5 or 6.

Compounds or pharmaceutically acceptable salts thereof have the following general formula I, II or III,

I

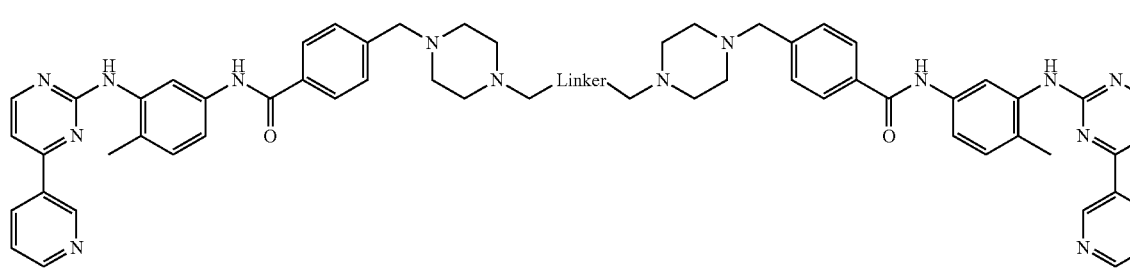

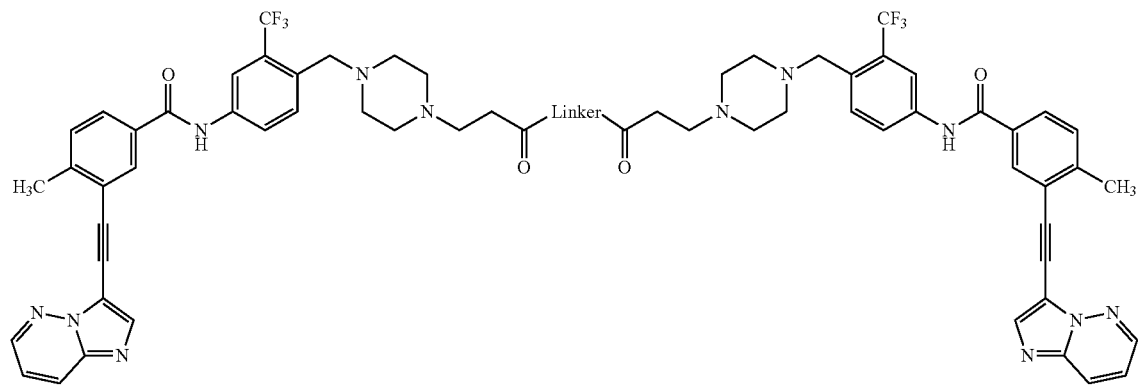

II

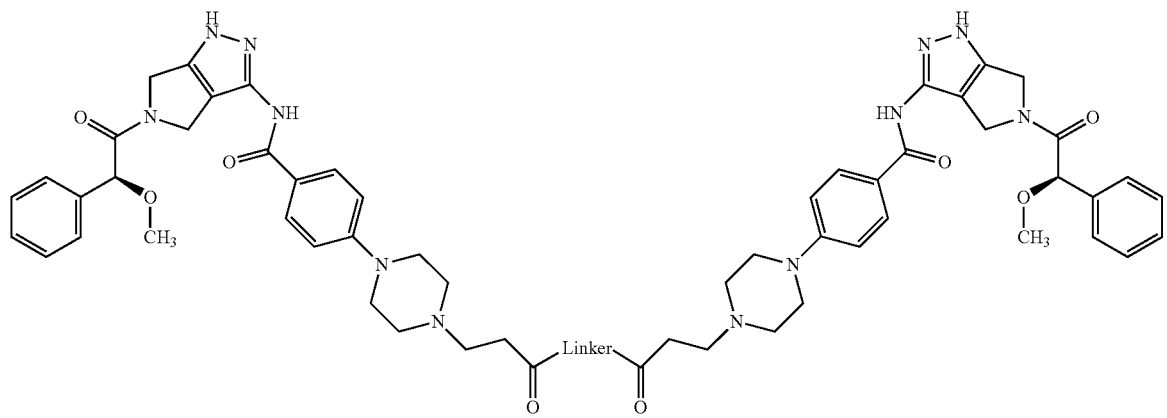

III

The compounds or pharmaceutically acceptable salts thereof, wherein the linker is $(Z_1)_a$—$(Z_2)_b$—$(Z_3)_c$, in which, $Z_1$, $Z_2$ and $Z_3$ each independently represent $C(O)(CH_2)_d NH$, $CO(CH_2)_e C(O)$, $(CH_2CH_2)_f NHC(O)$, $(CH_2CH_2)_g$—$C(O)NH$, $(CH_2)_h C(O)(OCH_2CH_2)_i NHC(O)(CH_2)_j C(O)$, $NH(CH_2)_k (OCH_2CH_2)_l$—$O(CH_2)_m NH$, $(CH_2)_n C(O)(OCH_2CH_2)_o NH(C(O)(CH_2)_p NH)_q C(O)$-alkyl, $C(O)NH(CH_2)_r NHC(O)$—$(CH_2)_s C(O)(NHCH_2CH_2)_t NH(C(O)(CH_2)_u NH)_v$—$C(O)$-alkyl, a~v each independently represent 1 to 20.

The compounds or pharmaceutically acceptable salts thereof, wherein the compound is:

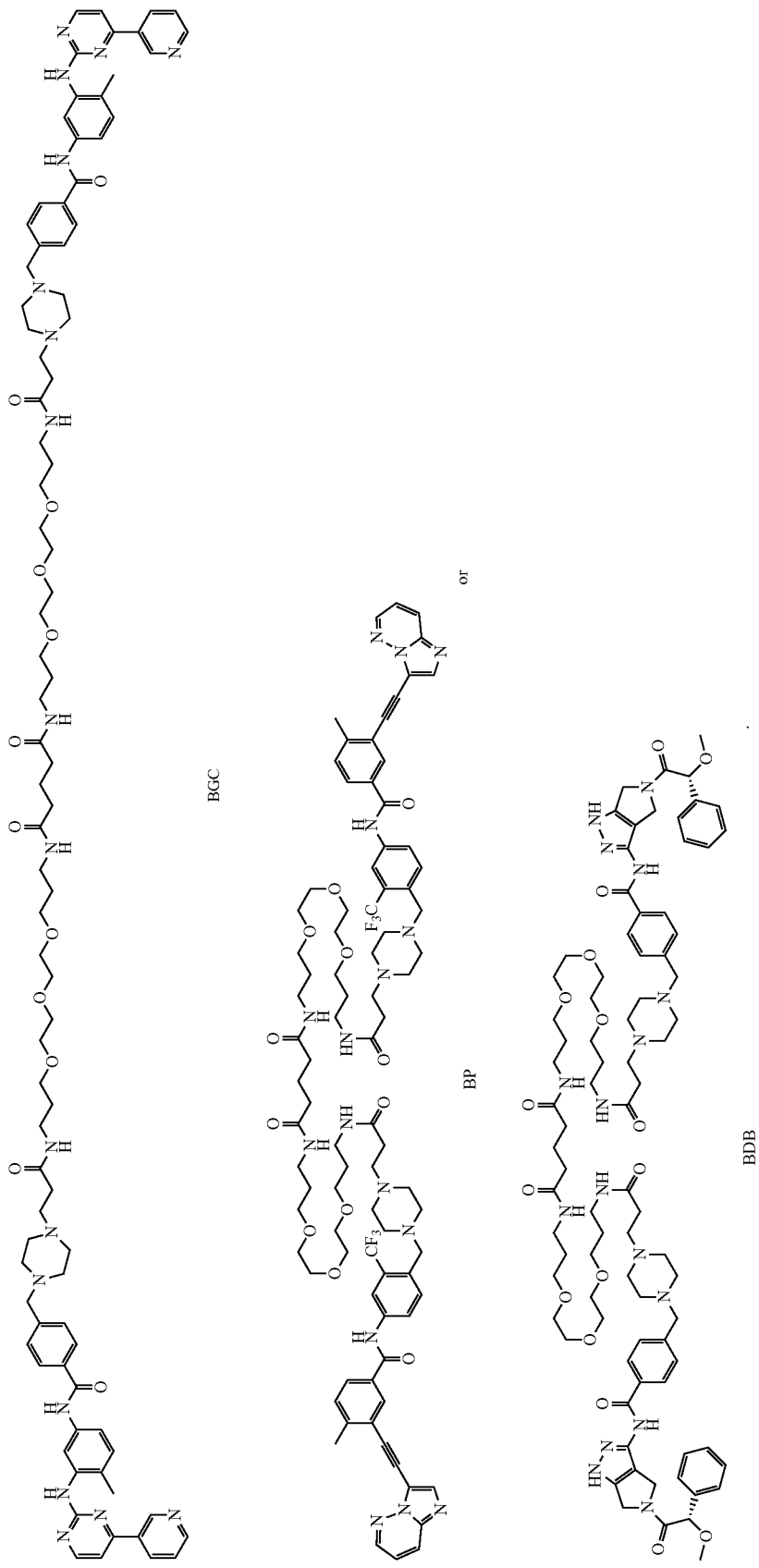

The present invention provides a method for synthesizing compounds of formula I, comprising:
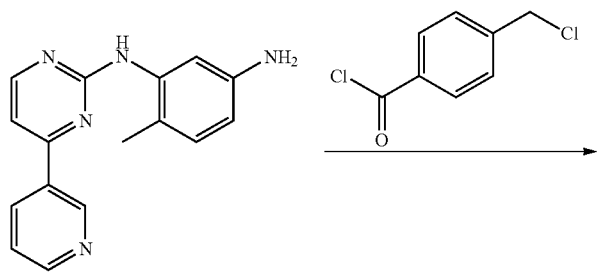
Compound 1a
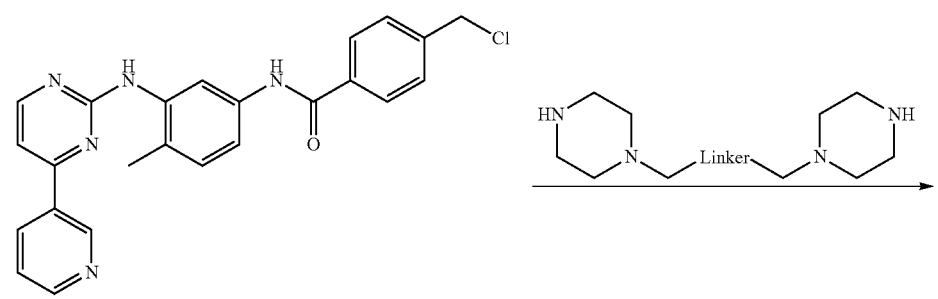
Compound 2a
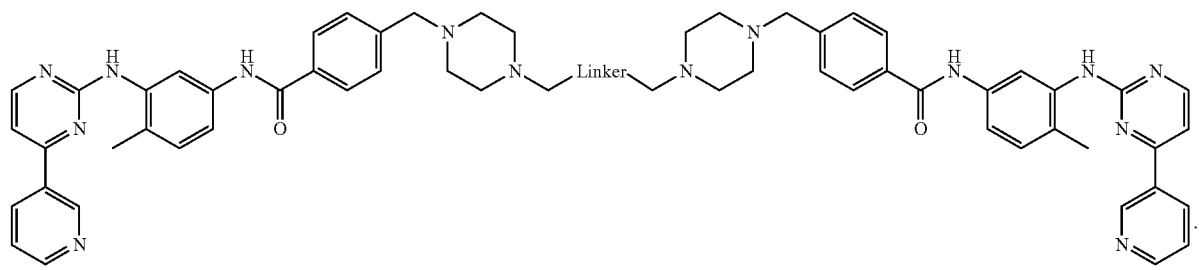
Compound I
The method for synthesizing compounds of formula I, comprising:
(1) Synthesis of compound 2a:
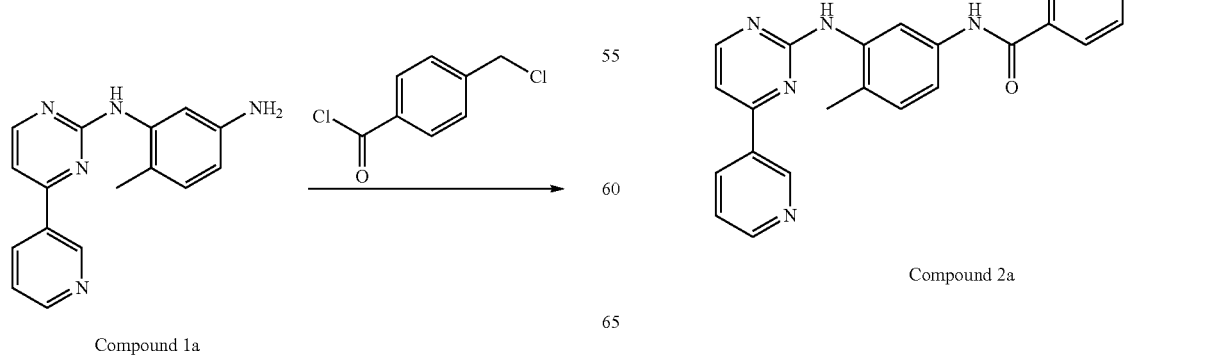
Compound 1a
Compound 2a
(2) Synthesis of compound BGC:

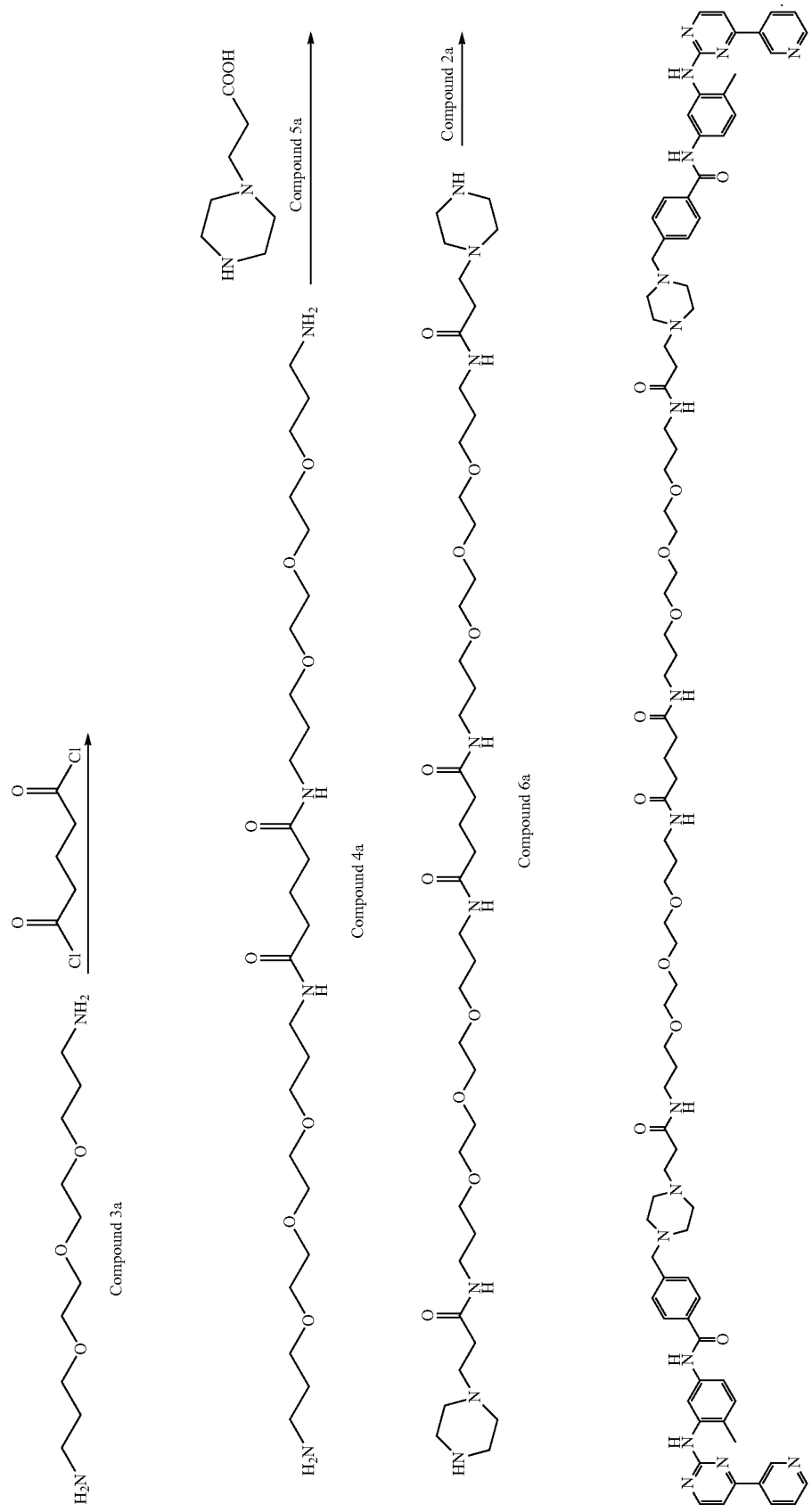

The method for synthesizing compounds of formula I, comprising:

(a) Synthesis of compound 2a compound 1a, triethylamine and 4-(chloromethyl) benzoyl chloride in dichloromethane, stirring at room temperature for 18 hours, then separating and purificating, to give a compound 2a;

(b) Synthesis of compound 6a

① Synthesis of compound 4a compound 3a, triethylamine and glutaryl dichloride in dichloromethane, stirring at room temperature for 6 hours, then separating and purificating, to give a compound 4a;

② Synthesis of compound 6a compound 4a, 1-hydroxy benzotrizole, 1-(3-dimethylaminopropyl)-3-ethylcarbodiimide hydrochloride and N-methylmorpholine in dichloromethane, reacting with ice bath for 0.5 hours, then adding compound 5a, reacting at room temperature, then separating and purificating, to give a compound 6a;

(c) Synthesis of compound BGC compound 2a, compound 6a and potassium carbonate N,N-dimethyl formamide, stirring at 100° C. for 18 hours, then separating and purificating, to give a compound BGC.

The method for synthesizing compounds of formula I, wherein, in step (a), the molar ratio of compound 1a, triethylamine and 4-(chloromethyl) benzoyl chloride is 18:35.6:21.3, the molar volume ratio of compound 1a and dichloromethane is 18:400 mmol/ml;

in step ① of (b), the molar ratio of compound 3a, triethylamine and glutaryl dichloride is 45.4:68.1:22.7, the molar volume ratio of compound 3a and dichloromethane is 45.4:300 mmol/ml;

in step ② of (b), the molar ratio of compound 4a, 1-hydroxy benzotrizole, 1-(3-dimethyl aminopropyl)-3-ethylcarbodiimide hydrochloride, N-methylmorpholine and compound 5a is 1:1.2:1.2:3:2.1, the molar volume ratio of compound 4a and dichloromethane is 1:20 mmol/ml;

in step (c), the molar ratio of compound 2a, compound 6a and potassium carbonate is 0.28:0.09:2.69, the molar volume ratio of compound 2a and N,N-dimethyl formamide is 0.28:20 mmol/ml.

The present invention provides a method for synthesizing compound BP, comprising:

(a) Synthesis of compound 12

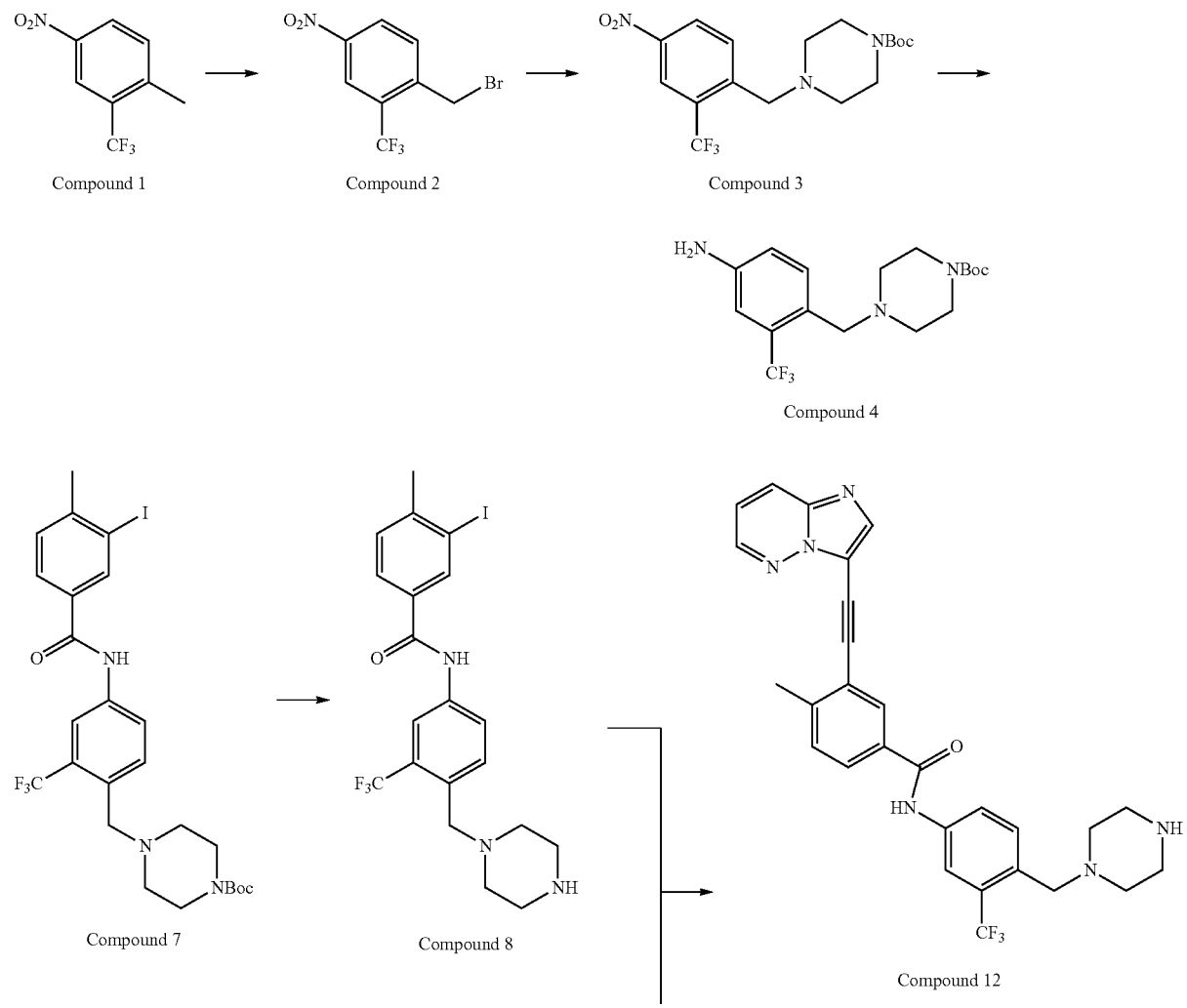

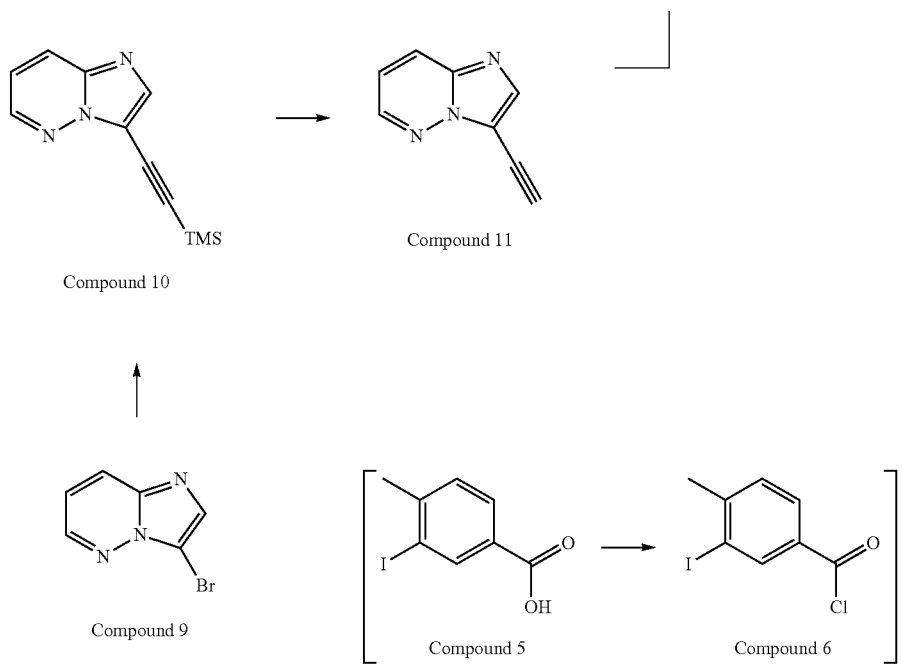
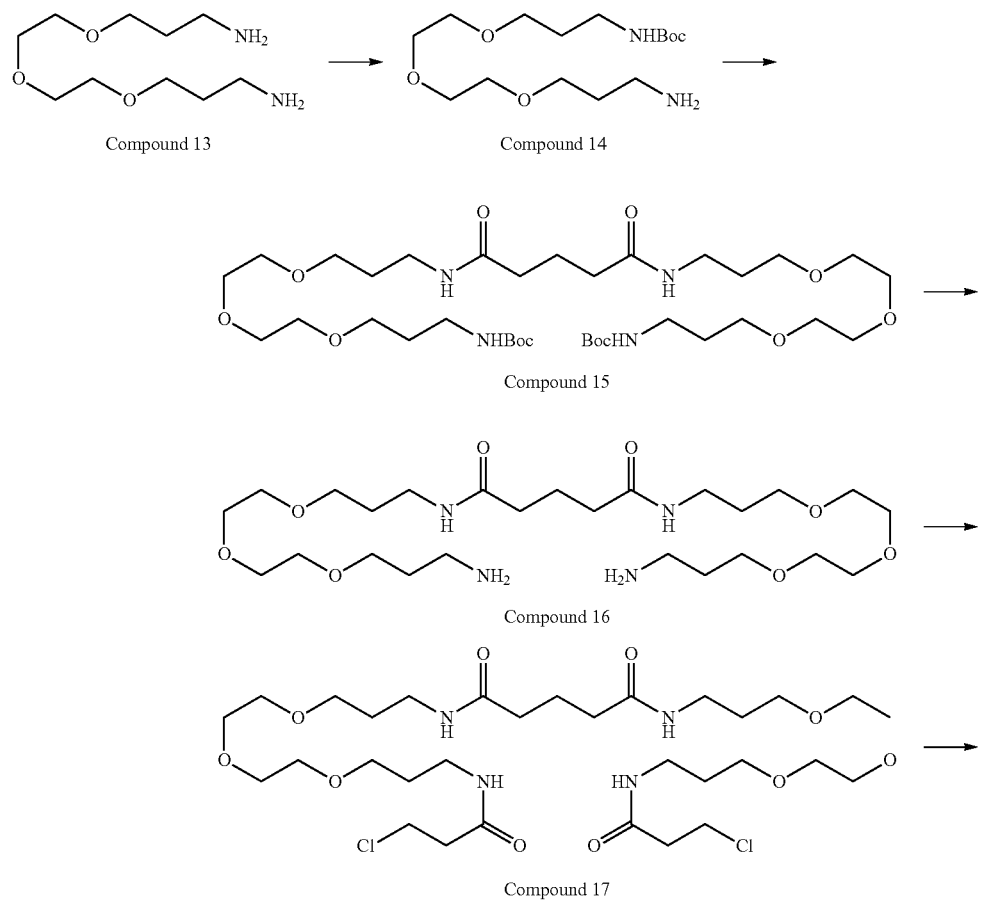
(b) Synthesis of compound BP

-continued

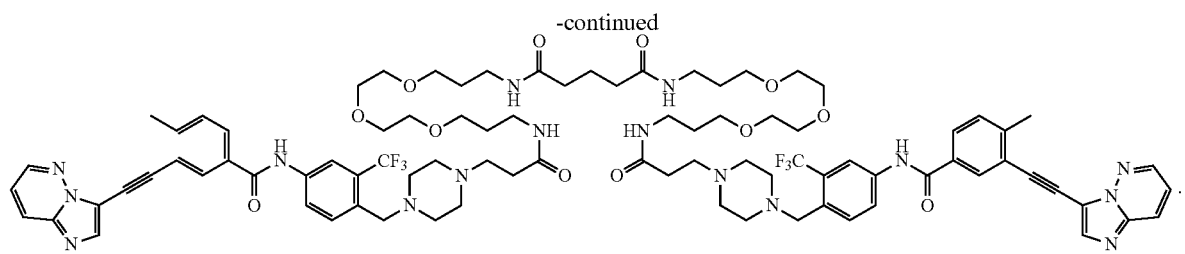

BP

The method for synthesizing compound BP, comprising:
i. Synthesis of compound 4
(1) 2-methyl-5-nitrobenzotrifluoride (compound 1) in carbontetrachloride, under protection of nitrogen, adding N-bromosuccinimide and 2,2'-azoisobutyronitrile, reacting with reflux for 24 hours, then separating, to give a compound 2;
(2) compound 2, N-boc-piperazine, and triethylamine in dichloromethane, stirring at room temperature for 3 hours, then separating and purificating, to give a compound 3;
(3) reduced iron powder, ammonium chloride, and compound 3 in mixture of water and ethanol, reacting with reflux for 1 hours, then separating and purificating, to give a compound 4;
ii. Synthesis of compound 8
(4) 3-iodo-4-methylbenzoic acid and thionyl chloride in mixture of tetrahydrofuran and N,N-dimethylformamide, reacting at 60° C. for 1 hours, then removing the solvent, to give a compound 6;
(5) compound 4, triethylamine and compound 6 in dichloromethane, reacting completely at room temperature, then separating and purificating, to give a compound 7;
(6) compound 7 with HCl in methanol, reacting completely, then removing the solvent, to give a compound 8;
iii. Synthesis of compound 11
(7) 3-bromoimidazo[1,2-b]pyridazine in acetonitrile, under protection of nitrogen, adding trans-dichlorobis(triphenylphosphine)palladium(II), cuprous iodide, dicyclohexylamine, and trimethylsilyl acetylene, reacting completely at 80° C., then separating and purificating, to give a compound 10;
(8) compound 10, methanol and saturated solution of potassium fluoride, reacting completely at room temperature, then separating and purificating, to give a compound 11;
iv. Synthesis of compound 12
(9) compound 8, compound 11 in N,N-dimethyl formamide, under protection of nitrogen, adding trans-dichlorobis(triphenylphosphine)palladium(II), cuprous iodide and N,N-diisopropylethylamine, reacting completely at room temperature, then separating and purificating, to give a compound 12;
v. Synthesis of compound 17
(10) compound 13, ditertbutyl pyrocarbonate in dichloromethane, reacting completely, then separating and purificating, to give a compound 14;
(11) compound 14, triethylamine and glutaryl dichloride in dichloromethane, stirring for 3 hours, then separating and purificating, to give a compound 15;
(12) compound 15 in HCl/ethylacetate, stirring at room temperature for 3 hours, then removing the solvent, to give a compound 16;
(13) compound 16, N,N-diisopropylethylamine and 3-chloropropionyl chloride in dichloromethane, stirring at room temperature for 3 hours, then removing the solvent, to give a compound 17;
vi. Synthesis of compound BP
(14) compound 12, compound 17 and triethylamine in tetrahydrofuran, reacting with reflux for 24 hours, then separating and purificating, to give a compound BP.

The method for synthesizing compound BP, wherein,
in step (1) of i, the molar ratio of 2-methyl-5-nitrobenzotrifluoride, N-bromosuccinimide, and 2,2'-azoisobutyronitrile is 0.15:0.16:0.01, the molar volume ratio of 2-methyl-5-nitrobenzotrifluoride and carbontetrachloride is 0.15:200 mmol/ml;
in step (2) of i, the molar ratio of compound 2, 1-boc-piperazine, and triethylamine is 0.146:0.16:0.22, the molar volume ratio of compound 2 and dichloromethane is 14.6:200 mmol/ml;
in step (3) of i, the molar ratio of reduced iron powder, ammonium chloride and compound 3 is 0.5:0.3:0.1, the molar volume ratio of compound 3 and the mixture is 0.1:200 mmol/ml, in the mixture, the volume ratio of water and ethanol is 1:1;
in step (4) of ii, the molar volume ratio of 3-iodo-4-methylbenzoic acid and the mixture is 0.09:101 mmol/ml, in the mixture, the volume ratio of tetrahydrofuran and N,N-dimethylformamide is 100:1;
in step (5) of ii, the molar ratio of compound 4, triethylamine and compound 6 is 0.08:0.12:0.088, the molar volume ratio of compound 4 and dichloromethane is 0.08:250 mmol/ml;
in step (6) of ii, the molar volume ratio of compound 7 and methanol is 0.03:100 mmol/ml;
in step (7) of iii, the molar volume ratio of 3-bromoimidazo[1,2-b]pyridazine and acetonitrile is 0.05:100 mmol/ml, the molar ratio of 3-bromoimidazo[1,2-b]pyridazine, trans-dichlorobis(triphenylphosphine)palladium(II), cuprous iodide, dicyclohexylamine, and trimethylsilyl acetylene is 0.05:0.0014:0.0014:0.06:0.6;
in step (8) of iii, the molar volume ratio of compound 10 and methanol is 0.04:50 mol/ml, the volume ratio of methanol and saturated solution of potassium fluoride is 50:20;
in step (9) of iv, the molar ratio of compound 8, compound 11, trans-dichlorobis(triphenylphosphine)palladium(II), cuprous iodide and N,N-diisopropylethylamine is 17.3:19:1:1:38, the molar volume ratio of compound 8 and N,N-dimethylformamide is 17.3:150 mmol/ml;
in step (10) of v, the molar ratio of compound 13 and ditertbutyl pyrocarbonate is 45.5:43.18, the volume ratio of compound 13 and dichloromethane is 45.5:600 mmol/ml;

in step (11) of v, the molar ratio of compound 14, triethylamine and glytaryl dichloride is 8.42:14.85:4.17, the molar volume ratio of compound 14 and dichloromethane is 8.42:120 mmol/ml;

in step (12) of v, the molar volume ratio of compound 15 and HCl/ethyl acetate is 3.8:100 mmol/ml, wherein the concentration of HCl/ethyl acetate is 2M;

in step (13) of v, the molar ratio of compound 16, N,N-diisopropylethylamine and 3-chloropropionyl chloride is 0.90:6.15:1.81, the molar volume ratio of compound 16 and dichloromethane is 0.90:50 mmol/ml;

in step (14) of vi, the molar ratio of compound 12, compound 17 and triethylamine is 0.2:0.1:0.3, the molar volume ratio of compound 12 and tetrahydrofuran is 0.2:10 mmol/ml.

The present invention provides a method for synthesizing compound BDB, comprising:

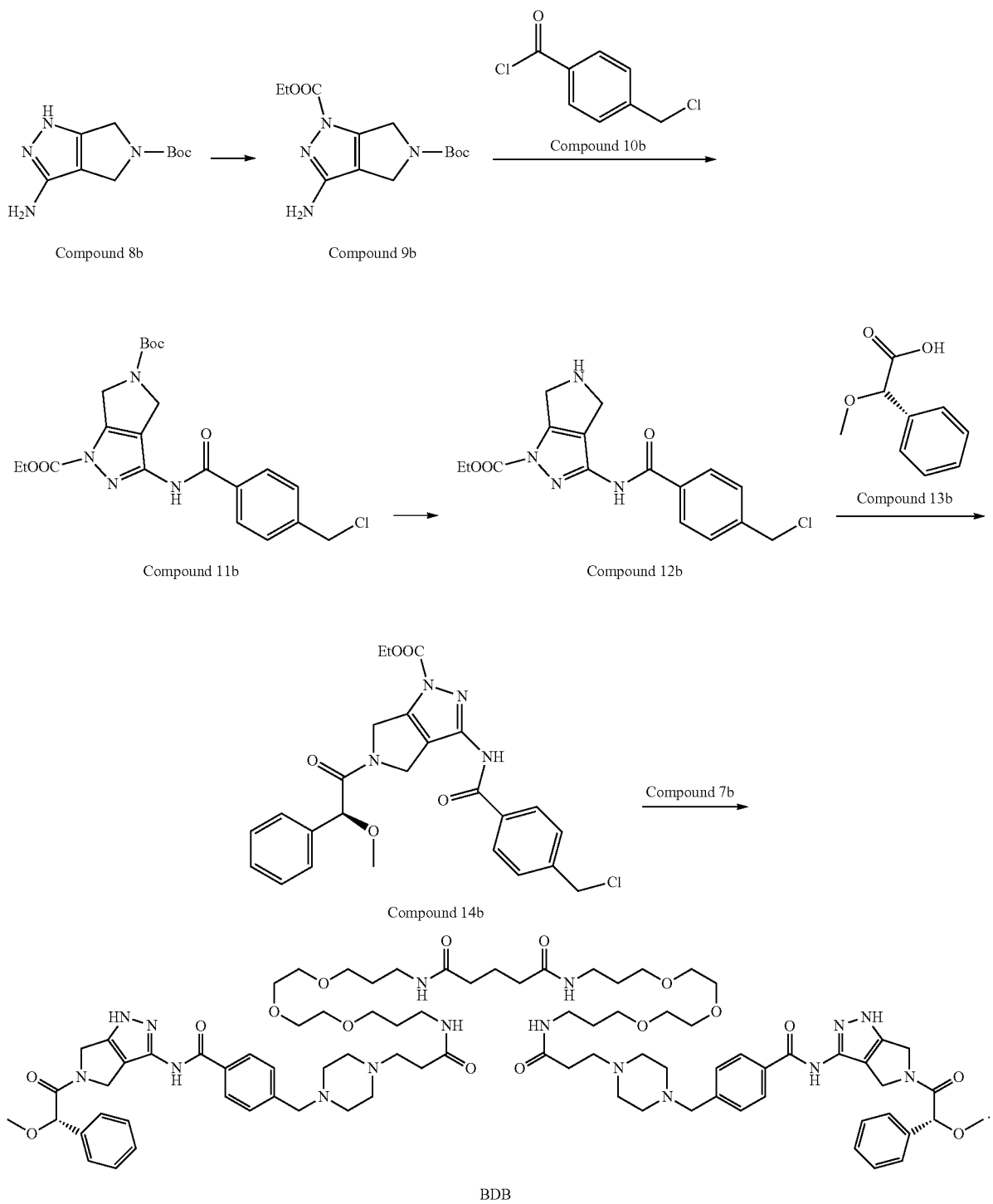

The method for synthesizing compound BDB, comprising:

A. Synthesis of compound 9b
ethyl chloroformate, compound 8b and N,N-diisopropylethylamine in tetrahydrofuran, stirring at room temperature for 16 hours, then separating and purificating, to give a compound 9b;

B. Synthesis of compound 11b
compound 9b, N,N-diisopropylethylamine, 4-chloromethylbenzoyl chloride in dichloromethane, stirring at room temperature for 16 hours, then separating and purificating, to give a compound 11b;

C. Synthesis of compound 12b
compound 11b in HCl/ethyl acetate, stirring at room temperature for 2 hours, then removing the solvent, to give a compound 12b;

D. Synthesis of compound 14b
compound 12b, compound 13b, 1-ethyl-3-(3-dimethylaminopropyl) carbodiimide hydrochloride, 1-hydroxybenzotriazole, and N,N-diisopropylethylamine in dichloromethane, stirring at room temperature for 16 hours, then separating and purificating, to give a compound 14b;

E. Synthesis of compound BDB
compound 7b, compound 14b and potassium carbonate in N,N-dimethylfomamide, stirring at 60° C. for 5 hours, then separating, to give a compound BDB.

The method for synthesizing compound BDB, wherein,
in step A, the molar ratio of ethyl chloroformate, compound 8b and N,N-diisopropylethylamine is 46.5:44.5:264, the molar volume ratio of ethyl chloroformate and tetrahydrofuran is 46.5:350 mmol/ml;
in step B, the molar ratio of compound 9b, N,N-diisopropylethylamine and 4-(chloromethyl)benzoyl chloride is 0.67:0.8:0.8, the molar volume ratio of compound 9b and dichloromethane is 0.67:50 mmol/ml;
in step C, the molar volume ratio of compound 11b and HCl/ethyl acetate is 0.445:20 mmol/ml, the concentration of HCl/ethyl acetate is 2M;
in step D, the molar ratio of compound 12b, compound 13b, 1-ethyl-3-(3-dimethylaminopropyl) carbodiimide hydrochloride, 1-hydroxybenzotriazole, N,N-diisopropylethylamineis 0.445:0.445:0.534:0.534:0.534, the molar volume ratio of compound 12b and dichloromethane is 0.445:25 mmol/ml;
in step E, the molar ratio of compound 7b, compound 14b and potassium carbonate is 0.4:1:4.8, the molar volume ratio of compound 7b and N,N-dimethylformamide is 0.4:50 mmol/ml.

The method for synthesizing compound BDB, wherein compound 7b is synthesed by the following method:

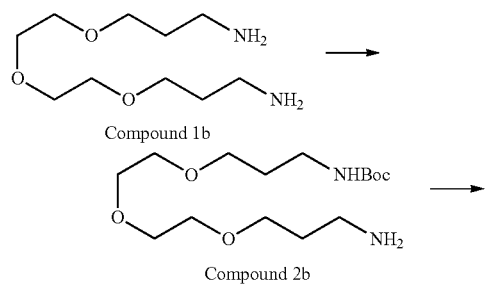

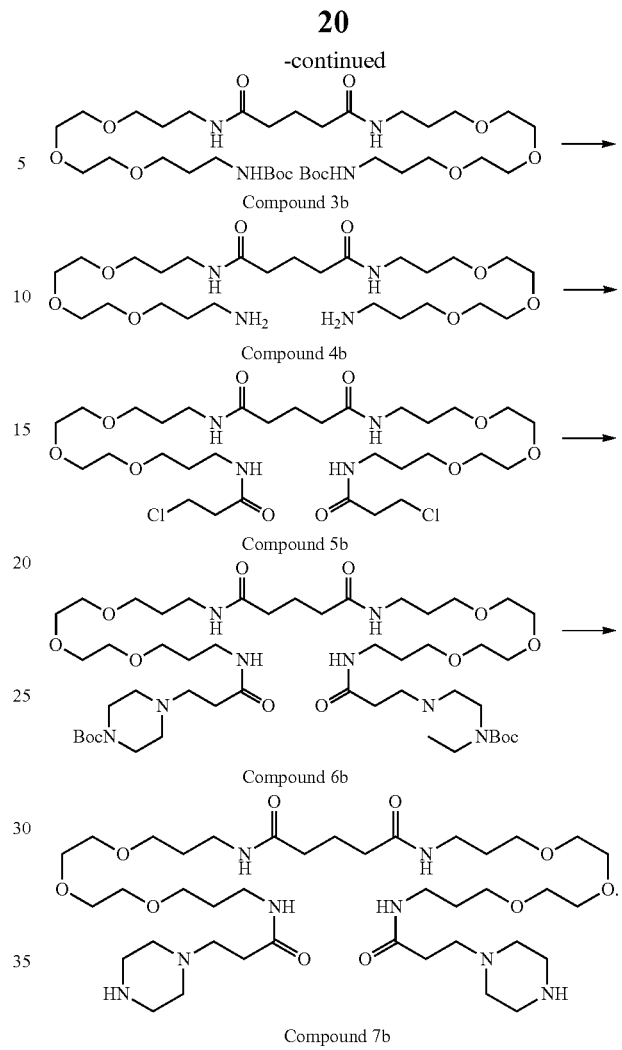

The method for synthesizing compound BDB, wherein compound 7b is synthesed by the following steps:

I. Synthesis of compound 2b
compound 1b and ditertbutyl pyrocarbonate in dichloromethane, reacting completely, then separating and purificating, to give a compound 2b;

II. Synthesis of compound 3b
compound 2b, triethylamine and glutaryl dichloride in dichloromethane, stirring at room temperature for 3 hours, then separating and purificating, to give a compound 3b;

III. Synthesis of compound 4b
compound 3b in HCl/ethyl acetate, stirring at room temperature for 3 hours, then removing the solvent, to give a compound 4b;

IV. Synthesis of compound 5b
compound 4b, N,N-diisopropylethylamine and 3-chloropropionyl chloride in dichloromethane, stirring at room temperature for 3 hours, then separating and purificating, to give a compound 5b;

V. Synthesis of compound 6b
compound 5b, 1-Boc-piperazine and N,N-diisopropylethylamine in dioxane, reacting with reflux for 18 hours, then separating and purificating, to give a compound 6b;

VI. Synthesis of compound 7b
compound 6b in HCl/ethyl acetate, stirring at room temperature for 2 hours, then removing the solvent, to give a compound 7b.

The method for synthesizing compound BDB, wherein,
in step I, the molar ratio of compound 1b and ditertbutyl pyrocarbonate is 45.5:43.18, the molar volume ratio of compound 1b and dichloromethane is 45.5:600 mmol/ml;
in step II, the molar ratio of compound 2b, triethylamine and glutaryl dichloride is 8.42:14.85:4.17, the molar volume ratio of compound 2b and dichloromethane is 8.42:120 mmol/ml;
in step III, the molar volume ratio of compound 3b and HCl/ethyl acetate is 3.8:100 mmol/ml, the concentration of HCl/ethyl acetate is 2M;
in step IV, the molar ratio of compound 4b, N,N-ethyl-diisopropylamine and 3-chloropropionyl chloride is 0.9:6.15:1.81, the molar volume ratio of compound 4b and dichloromethane is 0.9:50 mmol/ml;
in step V, the molar ratio of compound 5b, 1-Boc-piperazine and N,N-diisopropylethylamine is 0.14:2.68:0.77, the molar volume ratio of compound 5b and dioxane is 0.14:20 mmol/ml;
in step VI, the molar volume ratio of compound 6b and HCl/ethyl acetate is 0.1:20 mmol/ml, the concentration of HCl/ethyl acetate is 2M.

The use in preparing drugs for treatment of cell proliferation disorders of a compound of any one of compounds mentioned above or a pharmaceutically acceptable salt thereof.

Moreover, the drugs are tyrosine kinase inhibitor.
Moreover, the drugs are ABL inhibitor.
Moreover, the drugs are inhibitor of BCR-ABL or its mutant.
Moreover, the BCR-ABL mutant is T315I.
Moreover, the cell proliferation disorders are cancer.
Moreover, the cancer is chronic myelogenous leukemia, intestinal stromal tumors, gynecologic tumors, carina skin tumor, or, Ph+ALL.

The compounds or pharmaceutically acceptable salts in the present invention, as Bcr-Abl diploid inhibitors, which can effectively inhibit the tyrosine kinase activity; which can be effectively used to the treatment of the disease of abnormally active kinase; which have therapeutic effect of malignant tumors; the synthesis method is simple, with lower cost and better prospects.

Apparently, according to the present invention and the general technical knowledge in this field and the usual means, under the premise of not from this basic idea of the present invention, it can also make of other various modified, replaced or changed form.

Through the implementation of the following forms of specific embodiments, the present invention for further details of the above contents should not be understood as scope of this topic of the present invention limited to the following examples. The achievement by the present invention with above technologies is all within the scope of the present invention.

DESCRIPTION OF FIGURES

FIG. 1. Effection of the compound BGC in the present invention to the KBM5 tumor-bearing mice tumor volume

DETAILED DESCRIPTION OF THE INVENTION

The raw materials and instruments used in the present invention are all known products, which can be purchased commercially.

Abbreviated Name:
HOBT: 1-hydroxybenzotriazole; EDC: 1-(3-dimethylaminopropyl)-3-ethylcarbodiimide hydrochloride; NMM: N-methylmorpholine; DMSO: dimethyl sulfoxide; AIBN: 2,2'-azoisobutyronitrile; DMF: N,N-dimethylformamide; TLC: thin layer chromatography; DCM: dichloromethane; $(Boc)_2O$: ditertbutyl pyrocarbonate.

Example 1

Synthesis of Compound BGC

Synthesis routes as follows:

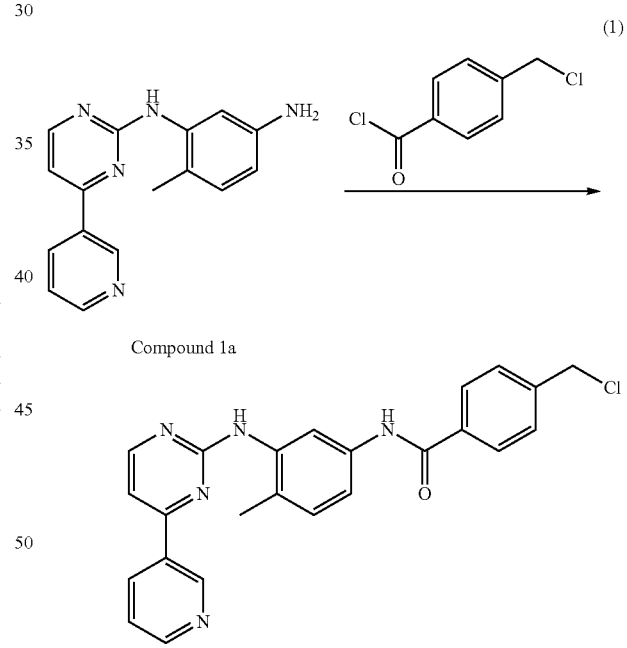

(2) Synthesis of Compound BGC:

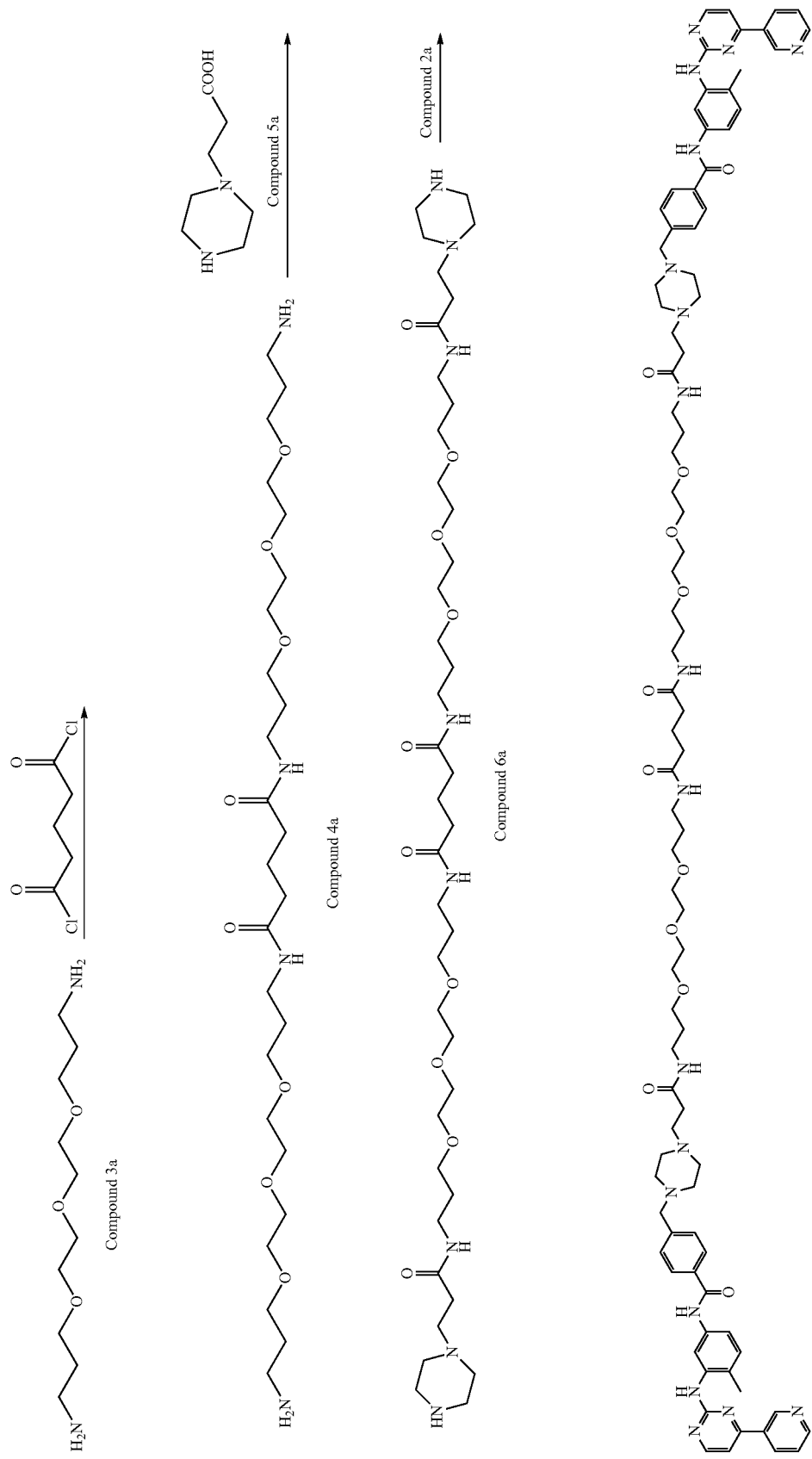

Detailed steps as follows:

a) Synthesis of Compound 2a

Compound 1a (5.0 g, 18.0 mmol; Manufacturer: Shanghai Xugang bio-tech limited company), and triethylamine (3.6 g, 35.6 mmol) were dissolved in dichloromethane (400 ml), 4-(chloromethyl)benzoyl chloride (4.0 g, 21.3 mmol) was dissolved in dichloromethane (100 ml), at 0° C., add the drops into the reaction solution, and end up to the room temperature, stir at room temperature for 18 hours, the solid precipitated, filtered and collected. Wash the solid with dichlomethane, then with water, to give the yellow solid compound 2a (5.3 g, 68% yield).

$^1$H NMR (400 MHz, DMSO-d6): δ 10.23 (s, 1 H), 9.28 (s, 1 H), 8.97 (s, 1 H), 8.69 (d, J=4.4 Hz, 1 H), 8.52 (m, 2 H), 8.09 (s, 1 H), 7.97 (d, J=7.6 Hz, 2 H), 7.59-7.42 (m, 5 H), 7.22 (d, J=8.0 Hz, 1 H), 4.84 (s, 2 H), 2.23 (s, 3 H). MS (ESI+) m/z: 430 [M+1]$^+$.

b) Synthesis of Compound 4a

At room temperature, compound 3a (10.0 g, 45.4 mmol, Manufacturer: Sigma-Aldrich) was dissolved in dichloromethane (250 ml), then triethylamine (6.9 g, 68.1 mmol) was added, glutaryl dichloride was dissolved in dichloromethane (50 ml), and added slowly into the reaction solution, stir at room temperature for 6 hours, wash with water (200 ml×2), dry the organic phase with sodium sulfate, vacuum evaporate the solvent, and purify the residues with silica gel column chromatography (dichloromethane/methanol=20/1), to give the compound 4a (4.3 g, 35.4% yield).

c) Synthesis Compound 6a

With ice bath, compound 4a (2.7 g, 5.0 mmol) was dissolved in dichloromethane (100 ml), then HOBT (0.81 g, 6.0 mmol), EDC (0.59 g, 6.0 mmol), NMM (1.52 g, 15 mmol) were added, react for half hour, compound 5a (1.67 g, 10.5 mmol, Manufacturer: J&K Scientific Limited Company) was added in batches into the reaction solution, gradually rise to the room temperature, react overnight, wash the organic phase of reaction solution with saturated sodium chloride (100 ml×2), dry the organic phase with sodium sulfate, vacuum evaporate the solvent, purify the residues with silica gel column chromatography, to give the compound 6a (1.3 g, 31.8% yield).

$^1$H NMR (400 MHz, D$_2$O), 3.62 (30H, m), 3.53 (14H, m), 3.21 (8H, q, J=7.2 Hz), 2.77 (4H, t, J=6.8 Hz), 2.21 (4H, t, J=7.6 Hz), 1.82 (2H, m).

d) Synthesis of Compound BGC

Compound 6a (72 mg, 0.09 mmol), compound 2a (120 mg, 0.28 mmol), K$_2$CO$_3$ (350 mg, 2.69 mmol), N,N-dimethylformamide (20 ml) were added into round flask, stirred at 100° C. for 18 hours, cool down to room temperature, pour the reaction solution into stirring ice water, precipitate the solid, filter, collect the solid. The residue purifys through the high efficient liquid phase, to give the orange solid BGC (18 mg, 12% yield).

$^1$H NMR (400 MHz, D$_2$O): δ 9.40 (s, 2 H), 9.12 (d, J=8 Hz, 2 H), 8.87 (d, J=5.2 Hz, 2 H), 8.50 (bs, 2H), 8.13 (t, J=6.8 Hz, 2 H), 7.95 (d, J=7.6 Hz, 4 H), 7.90 (s, 2 H), 7.65 (d, J=8 Hz, 4 H), 7.45 (d, J=5.2 Hz, 2 H), 7.36 (d, J=8 Hz, 2 H), 7.24 (d, J=7.6 Hz, 2 H), 4.43 (s, 4 H), 3.66-3.44 (m, 44 H), 3.28 (t, J=6.8 Hz, 4H), 3.22 (t, J=6.8 Hz, 4H), 2.78 (t, J=6.8 Hz, 4 H), 2.26 (s, 6 H), 2.22 (t, J=7.2 Hz, 4 H), 1.87-1.70 (m, 10 H). MS (ESI+) m/z: 1604 [M+1]$^+$.

Example 2

Synthesis of Compound BP

Synthesis routes as follows:

a. Synthesis of Compound 12

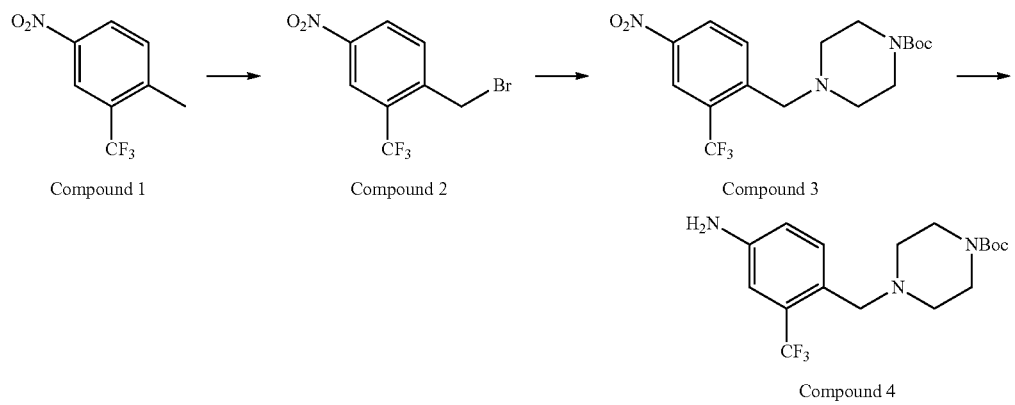

Compound 1     Compound 2     Compound 3

Compound 4

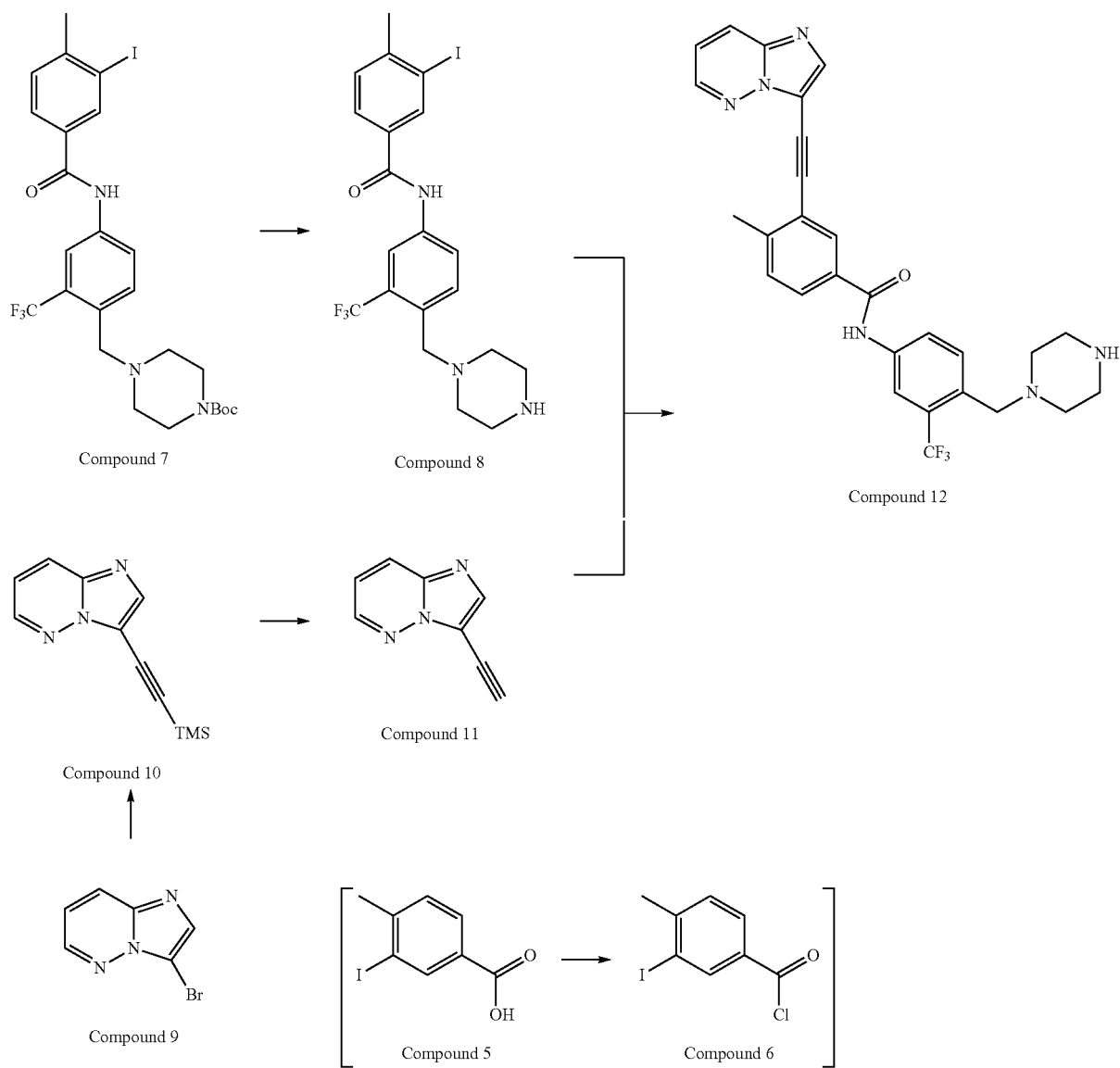
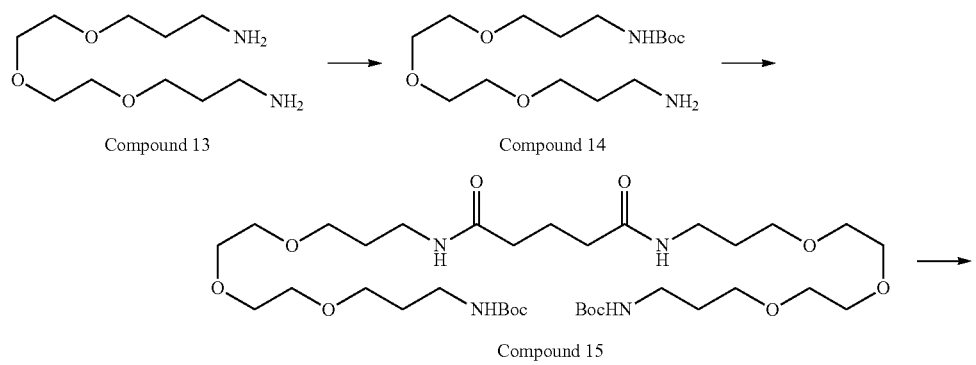
b. Synthesis of Compound BP

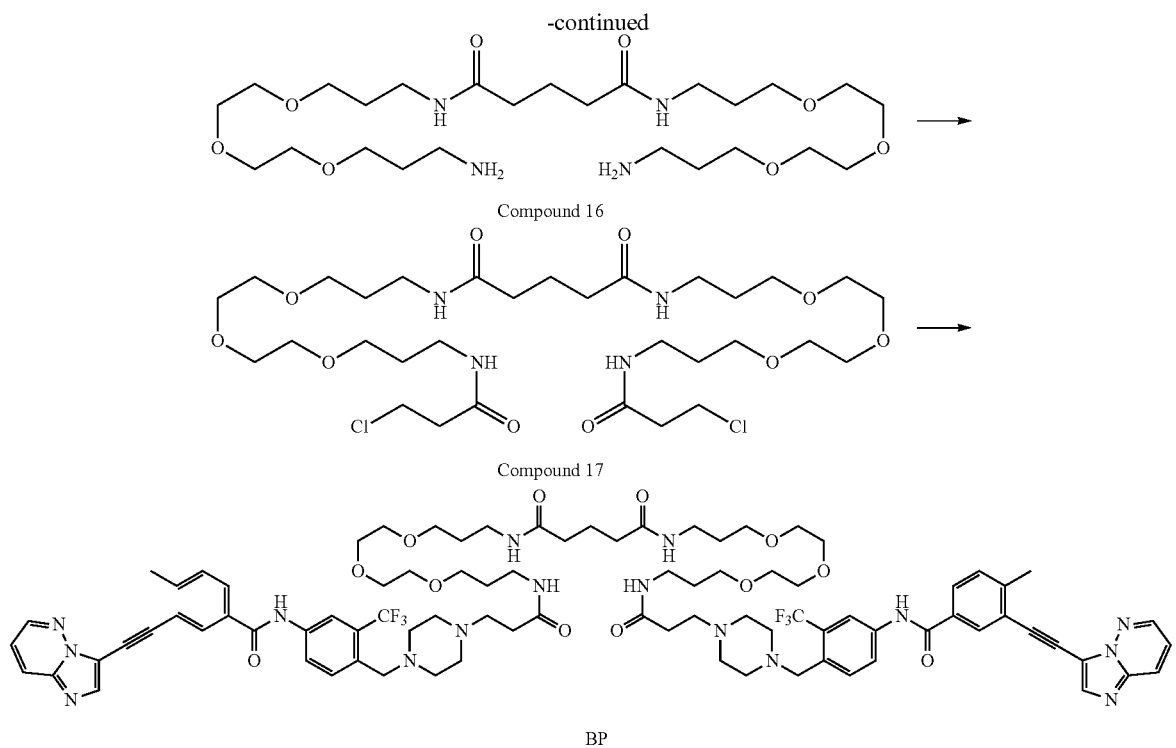

Synthesis of Compound 2

2-methyl-5-nitrobenzotrifluoride (compound 1: 30 g, 0.15 mol) was added into carbontetrachloride (200 ml), under protection of nitrogen, then N-bromosuccinimide (28.8 g, 0.16 mol) and AIBN (2.5 g, 0.01 mol) were added, electromagnetically mix, rise the temperature and reflux react for 24 hours, cool down to room temperature, filter the reaction solution. Wash the solid with ethyl acetate, collect the ethyl acetate phase, wash wish saturated sodium bicarbonate solution, then with sodium chloride solution (10 ml×2), dry with anhydrous sodium sulfate, evaporate the solvent, collect the yellow oil like residue (compound 2), without purification, used directly for the next step.

Synthesis of Compound 3

Compound 2 from the last step was dissolved into dichloromethane (200 ml), then N-Boc-piperazine (29.7 g, 0.16 mol) and triethylamine (30 ml, 0.22 mol) were added, stir at room temperature for 3 hours, then 100 ml Water was added, adjust the pH value to 2-3 with 1 N HCl, extract the water phase with dichloromethane (100 ml) of raw materials and the impurities, adjust the pH value of water phase with 1N sodium hydroxide solution to 9-10, extract the product with dichloromethane (50 ml×3). Wash the organic phase with saturated sodium chloride solution (10 ml×2), dry with anhydrous sodium sulfate, evaporate the solvent, collect the yellow oil-like liquid (compound 3: 48.1 g, count as compound 1, 84.4% yield).

ESI-MS m/z: 390.2 [M+H]$^+$;

$^1$HNMR (CDCl$_3$, 500 MHz) δ: 8.52 (d, J=1.5 Hz, 1H), 8.39 (d, J=8.5 Hz, 1H), 8.12 (d, J=8.5 Hz, 1H), 3.75 (s, 2H), 3.47 (s, 4H), 2.45 (s, 4H), 1.47 (s, 9H).

Synthesis of Compound 4

Reduced iron powder (28 g, 0.50 mol) and ammonium chloride (15.9 g, 0.30 mol) were added into the mixture solution of water (100 ml) and ethanol (50 ml), reflux react for 30 min. Then compound 3 (38.9 g, 0.10 mol) was dissolved into ethanol (50 ml), add drops into reaction solution, react for 1 hour, detect the end of reaction with TLC; cool down to room temperature, filter the solid, evaporate the ethanol, extract the product with ethyl acetate (50 ml×3), wash the organic phase with saturated sodium chloride solution (10 ml×2), dry with anhydrous sodium sulfate, evaporate the solvent, collect the yellow oil-like liquid (compound 4: 34.9 g; 97.3% yield).

ESI-MS m/z: 360.2 [M+H]$^+$;

$^1$HNMR (d$^6$-DMSO, 500 MHz) δ: 7.29 (d, J=8.5 Hz, 1H), 6.86 (d, J=2 Hz, 1H), 6.75 (dd, J=2, 8.5 Hz, 1H), 5.45 (s, 2H), 3.29 (br s, 4H), 2.26-2.28 (m, 4H), 1.38 (s, 9H).

Synthesis of Compound 6

3-iodo-4-methyl-benzoic acid (compound 5: 23.6 g, 0.09 mol) was added into THF (100 ml) and DMF (1 ml), then thionyl chloride (11.78 g, 0.099 mol) was added, rise the temperature to 60° C. for 1 hour, evaporate the solvent, to give 3-iodobenzoyl chloride (compound 6), used directly for the next step.

Synthesis of Compound 7

Compound 4 (28.7 g, 0.08 mol) was dissolved in dichloromethane (200 ml), then triethylamine (17 ml, 0.12 mol) was added; dilute the 3-iodobenzoyl chloride (compound 6) with dichloromethane (50 ml), with ice water bath, add drops into reaction solution, rise the temperature to room temperature, react for 1 hour, detect the end reaction point with TCL. Wash the reaction solution with saturated sodium bicarbonate solution (20 ml×3), wash the organic phase with saturated sodium chloride solution (20 ml×2), dry with anhydrous sodium sulfate for the yellow solid (compound 7: 39.7 g, 82.5% yield).

ESI-MS m/z: 604.2 [M+H]$^+$;

$^1$HNMR (CDCl$_3$, 500 MHz) δ: 8.32 (s, 1H), 7.91 (s, 2H), 7.88~7.92 (m, 2H), 7.75~7.79 (m, 2H), 7.30 (d, J=8 Hz, 1H), 3.62 (s, 2H), 3.42-3.44 (m, 4H), 2.48 (s, 2H), 2.39-2.41 (m, 4H), 1.46 (s, 9H).

Synthesis of Compound 8

Compound 7 (18 g, 0.03 mol) was dissolved in methanol (100 ml), gas in HCl, react completely, evaporate the solvent, to give the compound 8, use directly for the next step.

Synthesis of Compound 10

3-bromoimidazo[1,2-b]pyridazine (compound 9: 10 g, 0.05 mol) was dissolved in acetonitrile (100 ml), under protection of nitrogen, trans-dichlorobis(triphenylphosphine)palladium(II) (1.0 g, 1.4 mmol), cuprous iodide (0.3 g, 1.4 mmol), and dicyclohexylamine (11 ml, 0.06 mol) were added, rise the temperature to 80° C., then trimethylsilyl acetylene (8 ml, 0.6 mol) was added slowly into reaction solution, react for 1 hour, detect with TLC, cool down the reaction solution to room temperature, filter the solution, wash the solid with dichloromethane (200 ml), collect the organic phase, evaporate the solvent, add the residue into dichloromethane (100 ml), wash the organic phase with saturated sodium chloride solution (20 ml×2), dry with anhydrous sodium sulfate, evaporate the solvent for the product. Crystallize the product with ethyl acetate/petroleum ether, to give the black powder solid (compound 10:8.9 g, 81.8% yield).

$^1$HNMR (CDCl$_3$, 400 MHz) δ: 8.47 (dd, J=1.6, 4.4 Hz, 1H), 7.99 (s, 1H), 7.96 (dd, J=1.6, 9.2 Hz, 1H), 7.10 (dd, J=4.4, 9.2 Hz, 1H), 0.33 (s, 9H).

Synthesis of Compound 11

Compound 10 (8 g, 0.04 mol) was dissolved in methanol (50 ml), then saturated potassium fluoride solution (20 ml) was added, react at room temperature for 20 min, detect with TLC, evaporate the methanol, dissolve the residue with dichloromethane (100 ml), wash organic phase with saturated sodium chloride solution (30 ml×3), dry with sodium sulfate, evaporate the solvent, to give the brownish black powder solid (compound 11: 5.2 g, 98.4% yield).

ESI-MS m/z: 144.1 [M+H]$^+$;

$^1$HNMR (CDCl$_3$, 400 MHz) δ: 8.48 (dd, J=1.6, 4.4 Hz, 1H), 8.02 (s, 1H), 8.00 (dd, J=1.6, 9.2 Hz, 1H), 7.12 (dd, J=4.4, 9.2 Hz, 1H), 3.82 (s, 1H).

Synthesis of Compound 12

Compound 8 (10 g, 17.3 mmol) was added into DMF (100 ml), under protection of nitrogen, then trans-dichlorobis(triphenylphosphine)palladium(II) (0.7 g, 1 mmol), cuprous iodide (0.2 g, 1 mmol), and ethyldiisopropylamine (6.6 ml, 38 mmol) were added, stir at room temperature; dilute compound 11 (2.7 g, 19 mmol) with DMF (50 ml), add drops into reaction solution, react for 1 hour, detect with TLC; pour the reaction solution into water (300 ml), extract product with dichloromethane (50 ml×3), wash organic phase with saturated sodium chloride solution (20 ml×2), dry with sodium sulfate, evaporate the solvent for the product; crystallize the product with ethanol/petroleum ether, to give the yellow powder solid (compound 12: 7.7 g, 85.7% yield).

ESI-MS m/z: 519.2 [M+H]$^+$;

$^1$HNMR (d$^6$-DMSO, 500 MHz) δ: 10.57 (s, 1H), 8.73 (dd, J=1.5, 4.5 Hz, 1H), 8.28 (dd, J=1.5, 9.5 Hz, 1H), 8.24 (s, 1H), 8.22 (d, J=1.5, 2H), 8.07 (d, J=8 Hz, 1H), 7.95 (dd, J=1.5, 8 Hz, 1H), 7.73 (d, J=8.5 Hz, 1H), 7.55 (d, J=8.5 Hz, 1H), 7.40 (dd, J=4.5, 9.5 Hz, 1H), 3.54 (s, 2H), 2.75 (br s, 4H), 2.61 (s, 3H), 2.34 (br s, 4H), 1.23 (br s, 1H).

Synthesis of Compound 14

Compound 13 (10 g, 45.5 mmol) was dissolved in 500 ml DCM, at room temperature, (Boc)$_2$O (9.4 g, 43.18 mmol) was dissolved in 100 ml DCM, add drops into reaction solution, react overnight; add 200 ml water into reaction solution, adjust pH value to 3-4, extract the organic phase to remove the impurities, adjust the pH value of water phase to 10, then add saturated sodium chloride solution, extract the product, wash the organic phase with saturated sodium chloride solution (10 ml×6) to remove the unfinished raw materials, dry with sodium sulfate, evaporate the solvent, to give the colorless oil-like product (compound 14: 4.7 g, 34.1% yield).

$^1$H NMR (400 MHz, CDCl$_3$): δ 5.11 (br s, 1 H), 3.63-3.45 (m, 12 H), 3.21 (t, J=6.0 Hz, 2 H), 2.81 (t, J=6.4 Hz, 2 H), 1.77-1.42 (m, 6 H), 1.42 (s, 9 H).

Synthesis of Compound 15

At room temperature, compound 14 (2.7 g, 8.42 mmol), and triethylamine (1.5 g, 14.85 mmol) were dissolved in dichloromethane (100 ml), glutaryl dichloride (0.7 g, 4.17 mmol) was dissolved in dichloromethane (20 ml), add drops into reaction solution, add drops for 1 hour, stir at room temperature for 3 hours for reaction, wash organic phase with saturated sodium chloride solution (100 ml×2), dry organic phase with sodium sulfate, vacuum evaporate the solvent, purify the residue with silica gel layer chromatography (dichloromethane/methanol=20/1), to give the colorless oil-like product (compound 15: 3.1 g, 100% yield).

ESI-MS m/z: 737.4 [M+H]$^+$;

$^1$H NMR (400 MHz, CDCl$_3$): δ 6.55 (br s, 2 H), 5.06 (br s, 2 H), 3.63-3.49 (m, 24 H), 3.34 (m, 4 H), 3.20 (m, 4 H), 2.22 (t, J=7.2 Hz, 4 H), 1.93 (m, 2 H), 1.78-1.70 (m, 8 H), 1.41 (s, 18 H).

Synthesis of Compound 16

Compound 15 (2.8 g, 3.80 mmol) was added in HCl/ethyl acetate (2 M, 100 ml), stir at room temperature for 3 hours, vacuum evaporate the solvent for the colorless oil-like liquid (compound 16: 2.6 g, around 100% yield), without purification, used directly for the next step.

Synthesis of Compound 17

At room temperature, compound 16 (484 mg, 0.90 mmol), and DIPEA (N,N-diisopropylethylamine: 800 mg, 6.15 mmol) were dissolved in dichloromethane (40 ml), dilute 3-chloropropionyl chloride (230 mg, 1.81 mmol) with dichloromethane (10 ml), add drops into reaction solution (more than 1 hour), stir at room temperature for 3 hours, wash the organic phase with saturated sodium chloride solution (50 ml×2), dry the organic phase with sodium sulfate, evaporate the solvent with lower pressure, add n-hexane to the residue and stir, filter, to give the white solid (compound 17: 330 mg, 50.9% yield).

$^1$H NMR (400 MHz, CDCl$_3$): δ 6.85 (bs, 2 H), 6.58 (bs, 2 H), 3.81 (t, J=6.4 Hz, 4 H), 3.66-3.53 (m, 24 H), 3.39-3.31 (m, 8 H), 2.64 (m, 4 H), 2.24 (t, J=7.2 Hz, 4 H), 1.81 (m, 2 H), 1.55-1.47 (m, 8 H).

Synthesis of Compound BP

Compound 12 (0.1 g, 0.2 mmol), compound 17 (0.07 g, 0.1 mmol), and triethylamine (42 μl, 0.3 mmol) were added in 10 ml tetrahydrofuran, reacting with reflux for 24 hours, evaporate the solvent, to give the yellow powder solid (compound BP: 63 mg, 37.5% yield).

ESI-MS m/z: 1681.8 [M+H]$^+$;

$^1$HNMR (D$_2$O, 400 MHz) δ: 8.48 (dd, J=1.6, 4.4 Hz, 2H), 8.03 (dd, J=1.6, 9.6 Hz, 2H), 7.99 (s, 2H), 8.97 (d, J=1.6, 4H), 7.82 (d, J=8 Hz, 2H), 7.71 (dd, J=1.6, 8 Hz, 2H), 7.48 (d, J=8.8 Hz, 2H), 7.31 (d, J=8.8 Hz, 2H), 7.15 (dd, J=4.4, 9.6 Hz, 2H), 3.66-3.44 (m, 44 H), 3.34 (s, 4H), 3.28 (t, J=6.8 Hz, 4H), 3.22 (t, J=6.8 Hz, 4H), 2.78 (t, J=6.8 Hz, 4 H), 2.26 (s, 6 H), 2.22 (t, J=7.2 Hz, 4 H), 1.87-1.70 (m, 10 H).

Example 3
Synthesis of Compound BDB
Synthesis routes as follows:
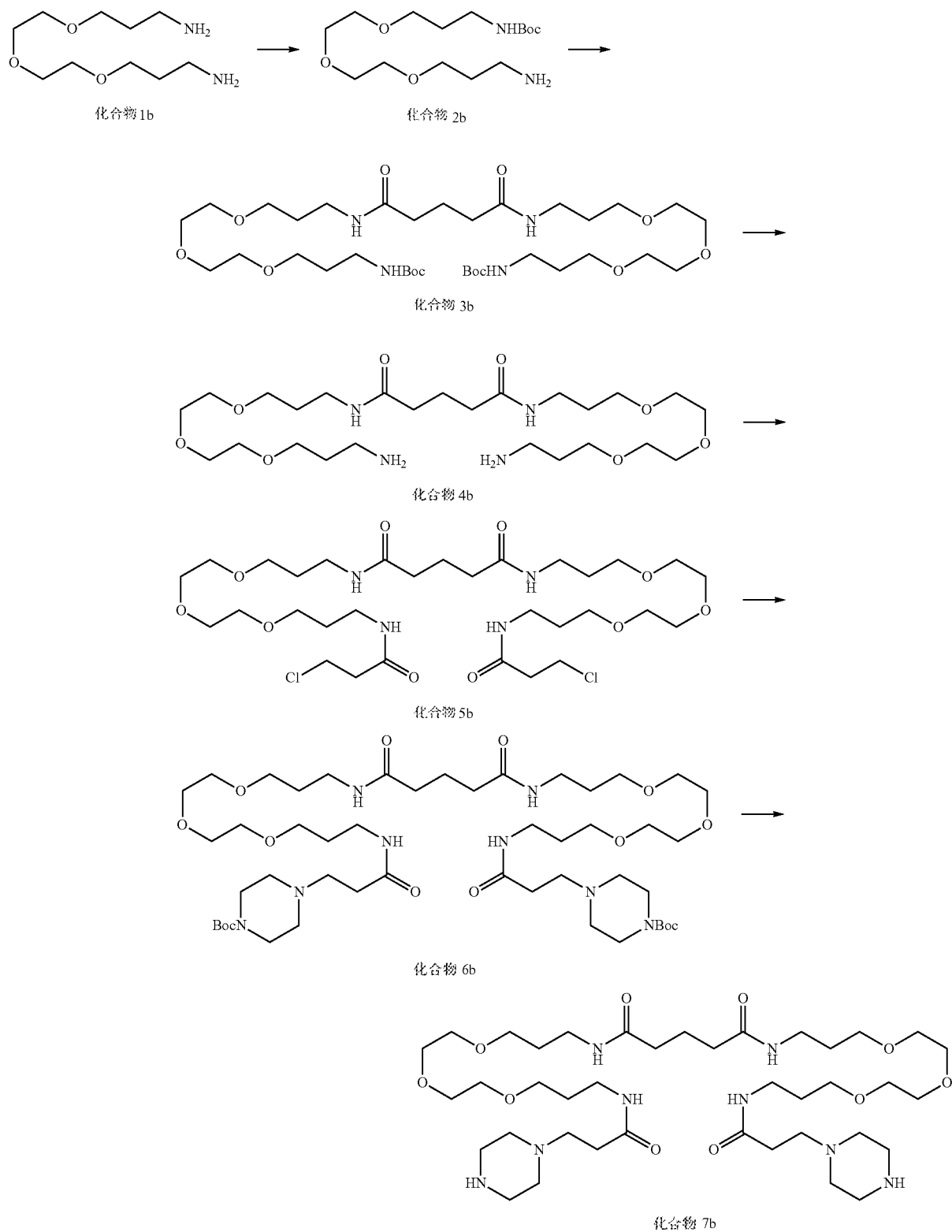

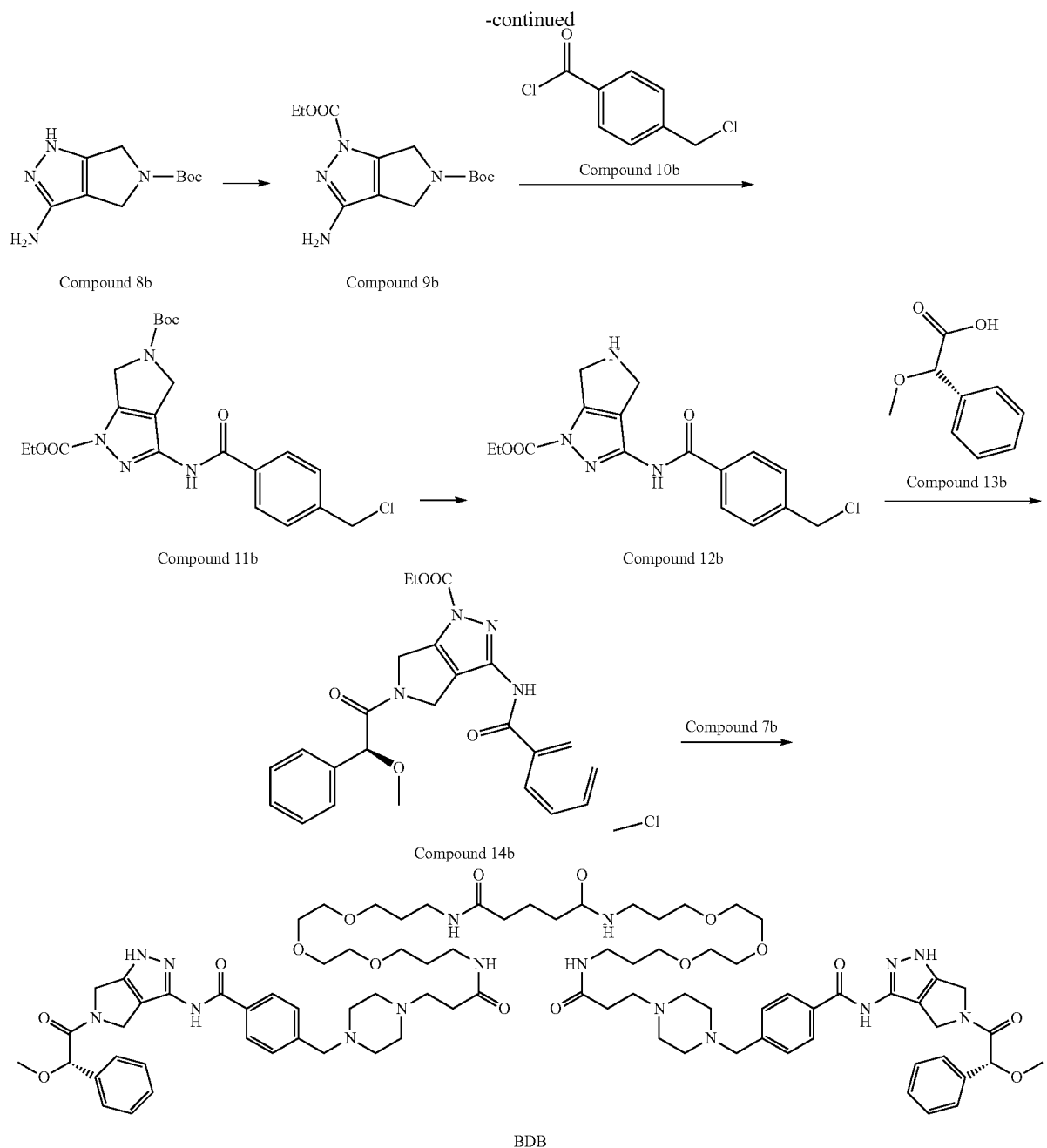

Detailed steps as following:

Synthesis of Compound 2b

Compound 1b (10 g, 45.5 mmol; manufacturer: Sigma-Aldrich) was dissolved in 500 ml DCM, at room temperature, (Boc)₂O (9.4 g, 43.18 mmol) was dissolved in 100 ml DCM, add drops into reaction solution, react overnight; add 200 ml water into reaction solution, adjust pH value to 3-4, extract the organic phase to remove the impurities, adjust the pH value of water phase to 10, add saturated sodium chloride solution, extract the product, wash the organic phase with saturated sodium chloride solution (10 ml×6) to remove the unfinished raw materials, dry with sodium sulfate, evaporate the solvent, to give the colorless oil-like product (compound 2b: 4.7 g, 34.1% yield).

¹H NMR (400 MHz, CDCl₃): δ 5.11 (bs, 1 H), 3.63-3.45 (m, 12 H), 3.21 (t, J=6.0 Hz, 2 H), 2.81 (t, J=6.4 Hz, 2 H), 1.77-1.42 (m, 6 H), 1.42 (s, 9 H).

Synthesis of Compound 3b

At room temperature, compound 2b (2.7 g, 8.42 mmol), and triethylamine (1.5 g, 14.85 mmol) were dissolved in dichloromethane (100 ml). Glytaryl dichloride (0.7 g, 4.17 mmol) was dissolved in dichloromethane (20 ml), add drops into reaction solution (more than 1 hour), stir at room temperature for 3 hours, wash the organic phase with saturated sodium chloride solution (100 ml×2), dry the organic phase with sodium sulfate, vacuum evaporate the solvent, purify the residue with silica gel layer chromatography (dichloromethane/methanol=20/1), to give the colorless oil-like product (compound 3b: 3.1 g, 100% yield).

ESI-MS m/z: 737.4 [M+H]$^+$;

$^1$H NMR (400 MHz, CDCl$_3$): δ 6.55 (bs, 2 H), 5.06 (bs, 2 H), 3.63-3.49 (m, 24 H), 3.34 (m, 4 H), 3.20 (m, 4 H), 2.22 (t, J=7.2 Hz, 4 H), 1.93 (m, 2 H), 1.78-1.70 (m, 8 H), 1.41 (s, 18 H).

Synthesis of Compound 4b

Compound 3b (2.8 g, 3.80 mmol) was added in HCl/ethyl acetate (2M, 100 ml), at room temperature, stir for 3 hours, vacuum evaporate the solvent for the colorless oil-like liquid (compound 4b: 2.6 g, around 100% yield), without purification, used directly for the next step.

Synthesis of Compound 5b

At room temperature, compound 4b (484 mg, 0.90 mmol), and DIPEA (800 mg, 6.15 mmol) were dissolved in dichloromethane (40 ml). Dilute 3-chloropropionyl chloride (230 mg, 1.81 mmol) with dichloromethane (10 ml), add drops into reaction solution (more than 1 hour), stir at room temperature for 3 hours, wash the organic phase with saturated sodium chloride solution (50 ml×2), dry the organic phase with sodium sulfate, evaporate the solvent with lower pressure, add n-hexane into the residue, stir, filter, to give the white solid (compound 5b: 330 mg, 50.9% yield).

$^1$H NMR (400 MHz, CDCl$_3$): δ 6.85 (bs, 2 H), 6.58 (bs, 2 H), 3.81 (t, J=6.4 Hz, 4 H), 3.66-3.53 (m, 24 H), 3.39-3.31 (m, 8 H), 2.64 (m, 4 H), 2.24 (t, J=7.2 Hz, 4 H), 1.81 (m, 2 H), 1.55-1.47 (m, 8 H).

Synthesis of Compound 6b

Compound 5b (100 mg, 0.14 mmol), 1-Boc-piperazine (500 mg, 2.68 mmol), DIPEA (100 mg, 0.77 mmol) and 1,4-dioxane (20 ml), were added in round flask, reacting with reflux for 18 hours, cool down to the room temperature, evaporate the solvent with lower pressure, dissolve the residue with dichloromethane, wash the organic phase with saturated sodium chloride solution, dry the organic phase with sodium sulfate, evaporate the solvent with lower pressure, purify the residue with silica gel layer chromatography (dichloromethane/methanol=10/1), to give the colorless oil-like liquid (compound 6b: 50 mg, 35.2% yield).

$^1$H NMR (400 MHz, CDCl$_3$): δ 7.98 (bs, 2 H), 7.07 (bs, 2 H), 3.66-3.53 (m, 24 H), 3.46 (m, 8 H), 3.36-3.31 (m, 8 H), 2.71 (m, 4 H), 2.47 (m, 12 H), 2.27 (t, J=6.8 Hz, 4 H), 1.95 (m, 2 H), 1.79-1.75 (m, 8 H), 1.45 (s, 18 H).

Synthesis of Compound 7b

Compound 6b (100 mg, 0.10 mmol) was added in HCl/ethyl acetate (2M, 20 ml), at room temperature stir for 2 hours, vacuum evaporate the solvent, to give colorless oil-like liquid (compound 7b: 100 mg, around 100% yield).

$^1$H NMR (400 MHz, D$_2$O) δ 3.62 (m, 30H), 3.53 (m, 14H), 3.21 (q, J=7.2 Hz, 8H), 2.77 (t, J=6.8 Hz, 4H), 2.21 (t, J=7.6 Hz, 4H), 1.82 (m, 2H), 1.74 (m, 8H).

Synthesis of Compound 9b

Ethyl chloroformate (4.5 ml, 46.5 mmol) was dissolved in tetrahydrofuran (100 ml), with ice bath, compound 8b (10 g, 44.5 mmol) and DIPEA (46 ml, 264 mmol) were dissolved in tetrahydrofuran (250 ml), at 0-5° C. add the drops into reaction solution, then rise to the room temperature for reaction of 16 hours, then vacuum evaporate the reaction solution and dissolve the residue with ethyl acetate, and wash the organic phase with water, dry the organic phase with sodium sulfate, vacuum evaporate the solvent with lower pressure, purify the residue with silica gel layer chromatography (ethyl acetate:petroleum ester=1:3), to give the white solid (compound 9b: 8.0 g, 60.7% yield).

$^1$H NMR (400 MHz, CD3OD) δ 4.72 (s, 2H), 4.40 (q, J=7.2 Hz, 2H), 4.12 (d, J=7.2 Hz, 2H), 1.53 (s, 9H), 1.40 (t, J=6.8 Hz, 3H).

Synthesis of Compound 11b

Compound 9b (200 mg, 0.67 mmol), and DIPEA (103 mg, 0.8 mmol) were dissolved in dichloromethane (25 ml), and cool down with ice water; 4-(chloromethyl)benzoyl chloride (compound 10b: 151 mg, 0.8 mmol) was dissolved in dichloromethane (25 ml), add drops at 0-5° C. to the reaction solution, rise to the room temperature, and stir for 16 hours, vacuum evaporate the reaction solution and dissolve the residue with ethyl acetate, and wash the organic phase with water, dry the organic phase with sodium sulfate, evaporate the solvent with lower pressure, purify the residue with silica gel layer chromatography (ethyl acetate:petroleum ester=1:2), to give the yellow solid (compound 11b: 220 mg, 73% yield).

$^1$H NMR (400 MHz, CD3OD) δ 7.98 (d, J=8.4 Hz, 2H), 7.60 (d, J=7.6 Hz, 2H), 4.74 (s, 2H), 4.69 (s, 4H), 4.50 (q, J=7.2 Hz, 2H), 1.55 (s, 9H), 1.45 (t, J=7.2 Hz, 3H).

Synthesis of Compound 12b

Compound 11b (200 mg, 0.445 mmol) was added in HCl/ethyl acetate (2M, 20 ml), at room temperature, stir for 2 hours, vacuum evaporate the solvent, to give the white solid (compound 12b: 172 mg, around 100% yield); without purification, used directly for the next step.

$^1$H NMR (400 MHz, CD3OD) δ 7.98 (d, J=8.0 Hz, 2H), 7.60 (d, J=8.0 Hz, 2H), 4.74 (s, 2H), 4.71 (s, 4H), 4.52 (q, J=7.2 Hz, 2H), 1.46 (t, J=7.2 Hz, 3H).

Synthesis of Compound 14b

At room temperature, compound 12b (153 mg, 0.445 mmol), compound 13b (74 mg, 0.445 mmol), EDCI (1-ethyl-3-(3-dimethylaminopropyl) carbodiimide hydrochloride: 91 mg, 0.534 mmol) and HOBT (72 mg, 0.534 mmol), were dissolved in dichloromethane (25 ml), then DIPEA (115 mg, 0.89 mmol) was added slowly into the reaction solution, stir for 16 hours, then add water to dilute the reaction solution. Extract the water phase with dichloromethane (100 ml×2), collect the organic phase and wash the organic phase with saturated sodium chloride solution and dry the organic solution with sodium sulfate, evaporate the solvent with lower pressure, purify the residue with silica gel layer chromatography (ethyl acetate:petroleum ester=1:1), to give the yellow solid (compound 14b: 100 mg, 45% yield).

$^1$H NMR (400 MHz, CD$_3$OD) δ 7.96 (d, J=8.0 Hz, 2H), 7.59 (d, J=8.0 Hz, 2H), 7.37~7.48 (m, 4H), 5.13 (s, 1H), 4.69~4.79 (m, 6H), 4.50 (q, J=7.2 Hz, 2H), 3.44 (s, 3H), 1.46 (t, J=7.2 Hz, 3H).

Synthesis of Compound BDB

Compound 7b (327 mg, 0.4 mmol), compound 14b (500 mg, 1 mmol), K$_2$CO$_3$ (664 mg, 4.8 mmol), and N,N-dimethylformamide (50 ml), were added in a round flask, at 60° C. stir for 5 hours, cool down to room temperature, pour the reaction solution into 200 ml water, extract the water phase with ethyl acetate, collect the organic phase, and wash the organic phase with saturated sodium chloride solution, dry the organic phase with sodium sulfate, evaporate the solvent with lower pressure, to give light yellow liquid (compound BDB: 522 mg, 81% yield).

$^1$H NMR (400 MHz, D2O) δ 7.77 (d, J=7.2 Hz, 2H), 7.68 (d, J=8 Hz, 2H), 7.47 (d, J=7.2 Hz, 2H), 7.43 (d, J=7.6 Hz, 2H), 7.35 (bs, J=7.2 Hz, 10H), 5.01 (s, 1H), 4.98 (s, 1H, s), 4.38 (s, 4H), 3.54~3.42 (m, 44H), 3.27~3.26 (bs, 6H), 3.11 (t, J=6.8 Hz, 4H), 3.04 (t, J=6.8 Hz, 4H), 2.66 (bs, 4H), 2.05 (m, 4H), 1.75~1.54 (m, 10 H).

Example 4

The Medicinal Activity of the Compound BGC

1. Tyrosine Kinase Inhibition

Reference: Amy Card et al., *Journal of Biomolarcular Screening* 14 (1) 2009; Jude Dunne et al., *Assay & Drug Development Technologies* Vol. 2, No. 2, 2004.

Using the method of mobility Shift Assay, detect activity of the compound BGC with kinase Abl in vitro. The concentration of BGC was diluted from 100 µM with 100% DMSO to 0.005 µM using 3 times dilution method, 10 concentrations in total for detection (2 duplicate) with staurosporine as standard control, set solvent control (10% DMSO) and negative control (EDTA).

Detect activity of different concentrations of the compound BGC on 384 holes reaction plate by enzyme-linked immune response on the inhibition of the kinase Abl, read the conversion rate data on Caliper, and convert the conversion rate to inhibition rate.

$$\text{Percent inhibition}=(\text{max}-\text{conversion})/(\text{max}-\text{min})*100$$

Wherein, max is the conversion rate of DMSO control; min refers to the conversion rate of enzyme-free control.

According to inhibition rate of the concentrations, calculate the half inhibitory concentration $IC_{50}$ of the compound BGC to tyrosine kinase Abl.

Inhibition results are as follows:

$IC_{50}$ of compound BGC: 0.02 µM;

The results show that, the compound BGC of the present invention has a strong inhibitory activity to c-Abl tyrosine kinase.

2. KBM5 (Bcr-Abl Positive) Tumor Growth Inhibition Test In Vitro of the Compound BGC Using ATP method to determine the cell toxicity of compound BGC of the present invention. Adjust the KBM5 cells to a suitable cell density. 140 ul cell suspensions inoculated each hole on 96-well plate. The vaccination density of each species cell is: 2000-6000; then the cell culture plate is placed in the incubator for 24 hours so that it is attached on the wall holes. Using 3 times dilution method to prepare the solution of BGC compound with different concentrations, and add them into the correspond holes on 96-well plate with vaccination in advance, 10 µL of each hole, and its final concentrations are as follows: 100 µM, 33.3 µM, 11.1 µM, 3.70 µM, 1.23 µM, 0.41 µM, 0.14 µM, 0.046 µM, 0.015 µM. Duplicate 3 times of each concentration. After 72 hours incubation in 37° C. incubator, detect the cell proliferation of each hole with ATP method, and calculate the drug concentration to median lethal concentration $IC_{50}$ of KBM5 cells.

Results:

Cytotoxicity of tumor cells of compound BGC to KBM5 (human wild type Bcr-Abl) is as follows:

$IC_{50}$ of compound BGC: 9 µM;

The test results show that the compound BGC of the present invention at the cellular level has a strong inhibitory activity in vitro.

3. Leukemia Subcutaneous Xenograft Growth Inhibition Test of the Compound BGC

According to the test results of the growth inhibition in vitro, assess inhibitory effect of the BGC to transplant subcutaneously in C57BL/6(Es-1$^c$) nude mice with human leukemia KBM5 cells growth.

The dosage of the compound BGC of the present invention is: 80 mg/Kg, 160 mg/Kg, 350 mg/Kg, meanwhile set a positive control group (160 mg/Kg Imatinib) and a control group (normal saline), mice were dosed once a day per group, continually in two weeks, and detected of the volume of tumor.

Study tumor growth if it can be inhibited, slowed or cured. Twice a week or every other day, use a vernier caliper to measure the tumor size. The calculation formula of tumor volume: $V=0.5a \times b^2$, a, b respectively represent the long and short radius of the tumor.

Data analysis: T test is used for the comparison between the two groups; one-way ANOVA is used between three or more groups. If there is a significant difference of f value, multiple comparisons should be used additional to ANOVA analysis. Two-way ANOVA is used to analyze potential synergies of combined drug group. All data analysis use SPSS 17.0; $p<0.05$ is considered with a significant difference.

Test results: the KBM5 cell subcutaneous implanted tumor model in vivo pharmacodynamic study results of the compound BGC as shown in FIG. 1.

In the subcutaneous tumor model, the compound BGC of the present invention has anti-tumor efficacy, it has the same inhibitory effect with a dosage of 350 mg/kg as Imatinib of 160 mg/kg.

4. Preliminary Pharmacokinetic Study of the Compound BGC

After single intravenous dosage test in female C57BL/6 (Es-1$^c$) nude mice of the compound BGC, HPLC-MS method was used to quantitatively determine its main concentration and drug concentration in serum, to study the test drug distribution difference in blood and tissues of the female C57BL/6(Es-1$^c$) nude mice; Imtinib in comparison.

Experiment methods and procedures are as follows: female C57BL/6(Es-1$^c$) nude mice, weight 18-25 g, age 6-8 weeks, other, 3 female C57BL/6(Es-1$^c$) nude mice for blank samples, prepare for the standard curve for analysis. Intravenous dosage 1 mg/kg, delivery volume 5 mL/kg. Intravenous injection drug solution: DMSO:Solutol HS15:Saline=5:5:90, v/v/v. Build LC-MS/MS method, and use internal standard method to quantitatively determine the test drug concentration in blood and tissues, linear range 1-1000 ng/mL, quantitative lower range 1 ng/mL. Female C57BL/6(Es-1$^c$) nude mice after intravenous injection dosage collect about 20 µL bloods from the mouse tail vein at 0.25 h, 2 h, 8 h and 24 h, use $K_2EDTA$ anticoagulant. Use steamed water to dilute the blood sample in accordance with volume in 3 times and store the diluted blood sample at −70° C. for analysis. At the meanwhile, collect samples of hearts, liver, spleen, lungs, kidneys, stomach, small intestine, pancreas tissue etc., wash with normal saline, weighed and recorded after filter drain, and then stored at −70° C. for analysis. Thaw out the weighed tissues; add heart, liver, spleen, lungs, kidneys, stomach, small intestine, and pancreas into Bead-beater homogenate with 3 times PBS buffer salt. Bone marrow samples flushed with 0.3 mL PBS buffer salt, centrifuged at 12000 RPM for 5 minutes, remove 0.25 mL supernatant, and add the remaining cell samples into 150 mL PBS homogenate buffer.

Data analysis: use WinNonlin (version 6.2) software, based on non-compartmental model to calculate the pharmacokinetic parameters.

The results show that, the half-life of compound BGC in the present invention is 3.5 hours, far greater than the half-life of Imatinib (1.5 hours). Compare with Imatinib, the compound BGC of the present invention has very obvious advantages on pharmacokinetics after intravenous injection.

Example 5

The Medicinal Activity of the Compound BP

1. Inhibition of Tyrosine Kinase

Reference: Amy Card et al., *Journal of Biomolarcular Screening* 14 (1) 2009; Jude Dunne et al., *Assay & Drug Development Technologies* Vol. 2, No. 2, 2004.

Using the method of Mobility Shift Assay, detect activity of the compound BP with kinase Abl in vitro. The concentration of BP was diluted from 100 μM with 100% DMSO to 0.005 μM using 3 times dilution method, 10 concentrations in total for detection (2 duplicate) with staurosporine as standard control, set solvent control (10% DMSO) and negative control (EDTA).

Detect activity of different concentrations of the compound BP on 384 holes reaction plate by enzyme-linked immune response on the inhibition of the kinase Abl, read the conversion rate data on Caliper, and convert the conversion rate to inhibition rate.

$$\text{Percent inhibition}=(\text{max}-\text{conversion})/(\text{max}-\text{min})*100$$

Wherein, max is the conversion rate of DMSO control, min refers to the conversion rate of enzyme-free control.

According to inhibition rate of the concentrations, calculate the half inhibitory concentration $IC_{50}$ of the compound BP to tyrosine kinase c-Abl.

Inhibition results are as follows:

$IC_{50}$ of compound BP: 0.01 μM;

The results show that, the compound BP of the present invention has a strong inhibitory activity to c-Abl tyrosine kinase.

2. KBM5 (Bcr-Abl Positive) and KBM5R (T315I Mutation) Tumor Growth Inhibition Test in Vitro of the Compound BP Using ATP method to determine the cell toxicity of compound BP of the present invention. Adjust the KBM5 and KBM5R cells to a suitable cell density. 140 ul cell suspensions inoculated each hole on 96-well plate. The vaccination density of each species cell is: 2000-6000; then the cell culture plate is placed in the incubator for 24 hours so that it is attached on the wall holes. Using 3 times dilution method to prepare the solution of BP compound with different concentrations, and add them into the correspond holes on 96-well plate with vaccination in advance, 10 μL of each hole, and its final concentrations are as follows: 100 μM, 33.3 μM, 11.1 μM, 3.70 μM, 1.23 μM, 0.41 μM, 0.14 μM, 0.046 μM, 0.015 μM. Duplicate 3 times of each concentration. After 72 hours incubation in 37° C. incubator, detect the cell proliferation of each hole with ATP method and calculate the drug concentration to median lethal concentration $IC_{50}$ of KBM5 and KBM5R cells.

Results:

Cytotoxicity of tumor cells of compound BP to KBM5 (human wild type Bcr-Abl) is as follows:

$IC_{50}$ of compound BP: 2 μM;

Cytotoxicity of tumor cells of compound BP to KBM5R (Bcr-Abl T315I mutation) is as follows:

$IC_{50}$ of compound BP: 5 μM;

The test results show that the compound BP of the present invention at the cellular level has a strong inhibitory activity in vitro.

3. Leukemia Subcutaneous Xenograft Growth Inhibition Test of the Compound BP

According to the test results of the growth inhibition in vitro, select the minimum $IC_{50}$ of the compound BP of the present invention, assess inhibitory effect of the BP to transplant subcutaneously in C57BL/6(Es-1$^c$) nude mice with human leukemia KBM5 and KBM5R cells growth.

The dosage of the compound BP of the present invention is: 80 mg/Kg, 160 mg/Kg, 350 mg/Kg, meanwhile set a positive control group (160 mg/Kg Imatinib) and a control group (normal saline), mice were dosed once a day per group, continually in two weeks and detected of the volume of tumor.

Study tumor growth if it can be inhibited, slowed or cured. Twice a week or every other day, use a vernier caliper to measure the tumor size. The calculation formula of tumor volume: $V=0.5a \times b^2$, a, b respectively represent the long and short radius of the tumor.

Data analysis: T test is used for the comparison between the two groups; one-way ANOVA is used between three or more groups. If there is a significant difference of f value, multiple comparisons should be used additional to ANOVA analysis. Two-way ANOVA is used to analyze potential synergies of combined drug group. All data analysis use SPSS 17.0; $p<0.05$ is considered with a significant difference.

Test results: the KBM5 (Bcr-Abl positive) cell subcutaneous implanted tumor model in vivo of the compound BP has anti-tumor efficacy, it has the same inhibitory effect with a dosage of 80 mg/kg as Imatinib of 160 mg/kg. To KBM5R (Bcr-Abl T315I mutation) cell subcutaneous implanted tumor model in vivo has anti-tumor efficacy, where the Imatinib has no significant efficacy.

4. Preliminary Pharmacokinetic Study of the Compound BP

After single intravenous dosage test in female C57BL/6 (Es-1$^c$) nude mice of the compound BP, HPLC-MS method was used to quantitatively determine its main concentration and drug concentration in serum, to study the test drug distribution difference in blood and tissues of the female C57BL/6(Es-1$^c$) nude mice; Imtinib in comparison.

Experiment methods and procedures are as follows: female C57BL/6(Es-1$^c$) nude mice, weight 18-25 g, age 6-8 weeks, other, 3 female C57BL/6(Es-1$^c$) nude mice for blank samples, prepare for the standard curve for analysis. Intravenous dosage 1 mg/kg, delivery volume 5 mL/kg. Intravenous injection drug solution: DMSO:Solutol HS15:Saline=5:5:90, v/v/v. Build LC-MS/MS method and use internal standard method to quantitatively determine the test drug concentration in blood and tissues, linear range 1-1000 ng/mL, quantitative lower range 1 ng/mL. Female C57BL/6(Es-1$^c$) nude mice after intravenous injection dosage collect about 20 μL blood from the mouse tail vein at 0.25h, 2h, 8h and 24 h, use $K_2$EDTA anticoagulant. Use steamed water to dilute the blood sample in accordance with volume in 3 times and store the diluted blood sample at −70° C. for analysis. At the meanwhile, collect samples of hearts, liver, spleen, lungs, kidneys, stomach, small intestine, pancreas tissue etc., wash with normal saline, weighed and recorded after filter drain, and then stored at −70° C. for analysis. Thaw out the weighed tissues; add heart, liver, spleen, lungs, kidneys, stomach, small intestine, and pancreas into Beadbeater homogenate with 3 times PBS buffer salt. Bone marrow samples flushed with 0.3 mL PBS buffer salt, centrifuged at 12000 RPM for 5 minutes, remove 0.25 mL supernatant, and add the remaining cell samples into 150 mL PBS homogenate buffer.

Data analysis: use WinNonlin (version 6.2) software, based on non-compartmental model to calculate the pharmacokinetic parameters.

The results show that the half-life of compound BP in the present invention is 3.5 hours, far greater than the half-life of Imatinib (1.5 hours). Compare with Imatinib, the compound BP of the present invention has very obvious advantages on pharmacokinetics after intravenous injection.

Example 6

The Medicinal Activity of the Compound BDB

1. Inhibition of Tyrosine Kinase

Reference: Amy Card et al., *Journal of Biomolarcular Screening* 14 (1) 2009; Jude Dunne et al., *Assay & Drug Development Technologies* Vol. 2, No. 2, 2004.

Using the method of mobility Shift Assay, detect activity of the compound BDB with kinase Abl in vitro. The concentration of BDB was diluted from 100 μM with 100% DMSO to 0.005 μM using 3 times dilution method, 10 concentrations in total for detection (2 duplicate) with staurosporine as standard control, set solvent control (10% DMSO) and negative control (EDTA).

Detect activity of different concentrations of the compound BDB on 384 holes reaction plate by enzyme-linked immune response on the inhibition of the kinase Abl, read the conversion rate data on Caliper, and convert the conversion rate to inhibition rate.

$$\text{Percent inhibition}=(\text{max}-\text{conversion})/(\text{max}-\text{min})*100$$

where max is the conversion rate of DMSO control, min refers to the conversion rate of enzyme-free control.

According to inhibition rate of the concentrations, calculate the half inhibitory concentration $IC_{50}$ of the compound BDB to tyrosine kinase c-Abl.

Inhibition results are as follows:

$IC_{50}$ of compound BDB: 0.05 μM;

The results show that the compound BDB of the present invention has a strong inhibitory activity to c-Abl tyrosine kinase.

2. KBM5 (Bcr-Abl Positive) and KBM5R (T315I Mutation) Tumor Growth Inhibition Test in Vitro of the Compound BDB Using ATP method to determine the cell toxicity of compound BDB of the present invention. Adjust the KBM5 and KBM5R cells to a suitable cell density. 140 ul cell suspensions inoculated each hole on 96-well plate. The vaccination density of each species cell is: 2000-6000; then the cell culture plate is placed in the incubator for 24 hours so that it is attached on the wall holes. Using 3 times dilution method to prepare the solution of BDB compound with different concentrations, and add them into the correspond holes on 96-well plate with vaccination in advance, 10 μL of each hole, and its final concentrations are as follows: 100 μM, 33.3 μM, 11.1 μM, 3.70 μM, 1.23 μM, 0.41 μM, 0.14 μM, 0.046 μM, 0.015 μM. Duplicate 3 times of each concentration. After 72 hours incubation in 37° C. incubator, detect the cell proliferation of each hole with ATP method, and calculate the drug concentration to median lethal concentration $IC_{50}$ of KBM5 and KBM5R cells.

Results:

Cytotoxicity of tumor cells of compound BDB to KBM5 (human wild type Bcr-Abl) is as follows:

$IC_{50}$ of compound BDB: 7 μM;

Cytotoxicity of tumor cells of compound BDB to KBM5R (Bcr-Abl T315I mutation) is as follows:

$IC_{50}$ of compound BDB: 8.9 μM;

The test results show that the compound BDB of the present invention at the cellular level has a strong inhibitory activity in vitro.

3. Leukemia Subcutaneous Xenograft Growth Inhibition Test of the Compound BDB

According to the test results of the growth inhibition in vitro, select the minimum $IC_{50}$ of the compound BDB of the present invention, assess inhibitory effect of the BDB to transplant subcutaneously in C57BL/6(Es-1$^c$) nude mice with human leukemia KBM5 and KBM5R cells growth.

The dosage of the compound BDB of the present invention is: 80 mg/Kg, 160 mg/Kg, 350 mg/Kg, meanwhile set a positive control group (160 mg/Kg Imatinib) and control group (normal saline), mice were dosed once a day per group, continually in two weeks and detected of the volume of tumor.

Study tumor growth if it can be inhibited, slowed or cured. Twice a week or every other day, use a vernier caliper to measure the tumor size. The calculation formula of tumor volume: $V=0.5 \times a \times b^2$, a, b respectively represent the long and short radius of the tumor.

Data analysis: T test is used for the comparison between the two groups; one-way ANOVA is used between three or more groups. If there is a significant difference of f value, multiple comparisons should be used additional to ANOVA analysis. Two-way ANOVA is used to analyze potential synergies of combined drug group. All data analysis use SPSS 17.0; $p<0.05$ is considered with a significant difference.

Test results: the KBM5 (Bcr-Abl positive) cell subcutaneous implanted tumor model in vivo of the compound BDB has anti-tumor efficacy, it has the same inhibitory effect with a dosage of 80 mg/kg as Imatinib of 160 mg/kg. To KBM5R (Bcr-Abl T315I mutation) cell subcutaneous implanted tumor model in vivo has anti-tumor efficacy, where the Imatinib has no significant efficacy.

4. Preliminary Pharmacokinetic Study of the Compound BDB

After single intravenous dosage test in female C57BL/6 (Es-1$^c$) nude mice of the compound BDB, HPLC-MS method was used to quantitatively determine its main concentration and drug concentration in serum, to study the test drug distribution difference in blood and tissues of the female C57BL/6(Es-1$^c$) nude mice; Imtinib in comparison.

Experiment methods and procedures are as follows: female C57BL/6(Es-1$^c$) nude mice, weight 18-25 g, age 6-8 weeks, other, 3 female C57BL/6(Es-1$^c$) nude mice for blank samples, prepare for the standard curve for analysis. Intravenous dosage 1 mg/kg, delivery volume 5 mL/kg. Intravenous injection drug solution: DMSO:Solutol HS15:Saline=5:5:90, v/v/v. Build LC-MS/MS method and use internal standard method to quantitatively determine the test drug concentration in blood and tissues, linear range 1-1000 ng/mL, quantitative lower range 1 ng/mL. Female C57BL/6(Es-1ᶜ) nude mice after intravenous injection dosage collect about 20 μL bloods from the mouse tail vein at 0.25h, 2h, 8h and 24 h, use K₂EDTA anticoagulant. Use steamed water to dilute the blood sample in accordance with volume in 3 times and store the diluted blood sample at −70° C. for analysis. At the meanwhile, collect samples of hearts, liver, spleen, lungs, kidneys, stomach, small intestine, pancreas tissue etc., wash with normal saline, weighed and recorded after filter drain, and then stored at −70° C. for analysis. Thaw out the weighed tissues; add heart, liver, spleen, lungs, kidneys, stomach, small intestine, and pancreas into Bead-beater homogenate with 3 times PBS buffer salt. Bone marrow samples flushed with 0.3 mL PBS buffer salt, centrifuged at 12000 RPM for 5 minutes, remove 0.25 mL supernatant, and add the remaining cell samples into 150 mL PBS homogenate buffer.

Data analysis: use WinNonlin (version 6.2) software, based on non-compartmental model to calculate the pharmacokinetic parameters.

The results show that the half-life of compound BDB in the present invention is 3.8 hours, far greater than the half-life of Imatinib (1.5 hours). Compare with Imatinib, the compound BDB of the present invention has very obvious advantages on pharmacokinetics after intravenous injection.

In summary, the compounds or pharmaceutically acceptable salts in the present invention, as Bcr-Abl diploid inhibitors, which can effectively inhibit the tyrosine kinase activity; which can be effectively used to the treatment of the disease of abnormally active kinase; which have therapeutic effect of malignant tumors; the synthesis method is simple, with lower cost and better prospects.

We claim:

1. Compound having a formula R-Linker-R, or pharmaceutically acceptable salt thereof,
wherein R is

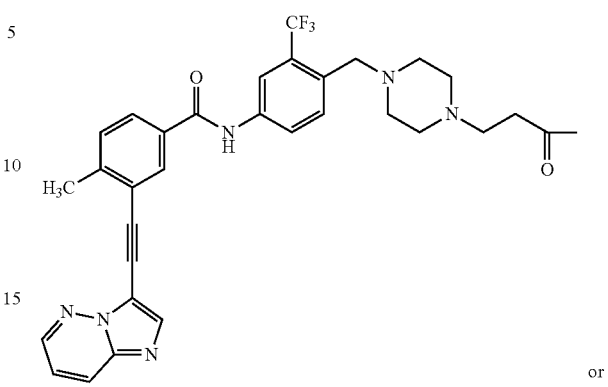

or

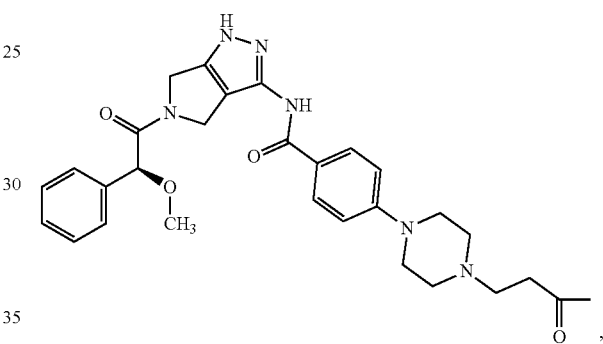

and, the Linker is $-(CH_2CH_2O)_{x3}-(CH_2)_{x2}-(NHCO)-(CH_2)_{x1}-(CONH)-(CH2)_{x2}-(OCH_2CH_2)_{x3}-$, in which, x1, x2 and x3 each independently is 1, 2, 3, 4, 5 or 6.

2. The compound or the pharmaceutically acceptable salt thereof according to claim 1, wherein the compound has formula I, formula II, or formula III,

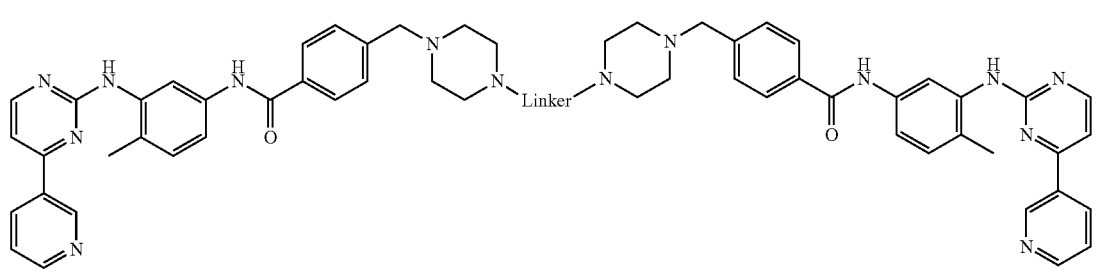

I

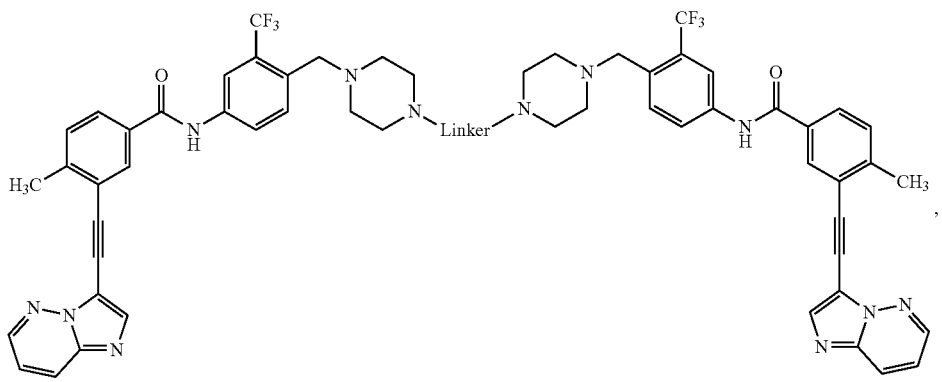

II

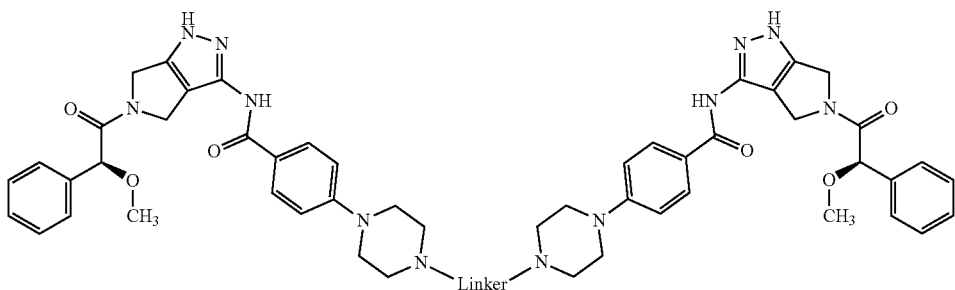

III

3. The compound or the pharmaceutically acceptable salt thereof according to claim 1, wherein the linker is $(Z_1)_a$—$(Z_2)_b$—$(Z_3)_c$, wherein $Z_1$, $Z_2$ and $Z_3$ each independently represents $C(O)(CH_2)_d NH$, $CO(CH_2)_e C(O)$, $(CH_2CH_2)_f NHC(O)$, $(CH_2CH_2)_g$—$C(O)NH$, $(CH_2)_h C(O)(OCH_2CH_2)_i NHC(O)(CH_2)_j C(O)$, $NH(CH_2)_k (OCH_2CH_2)_l$—$O(CH_2)_m$ NH, $(CH_2)_n C(O)(OCH_2CH_2)_o NH(C(O)(CH_2)_p NH)_q C(O)$—alkyl, or $C(O)NH(CH_2)_r NHC(O)$—$(CH_2)_s C(O)(NHCH_2CH_2)_t NH(C(O)(CH_2)_u NH)_v$—$C(O)$—alkyl, and wherein a to v each independently represents an integer from 1 to 20.

4. The compound or the pharmaceutically acceptable salt thereof according to claim 1, wherein the compound is:

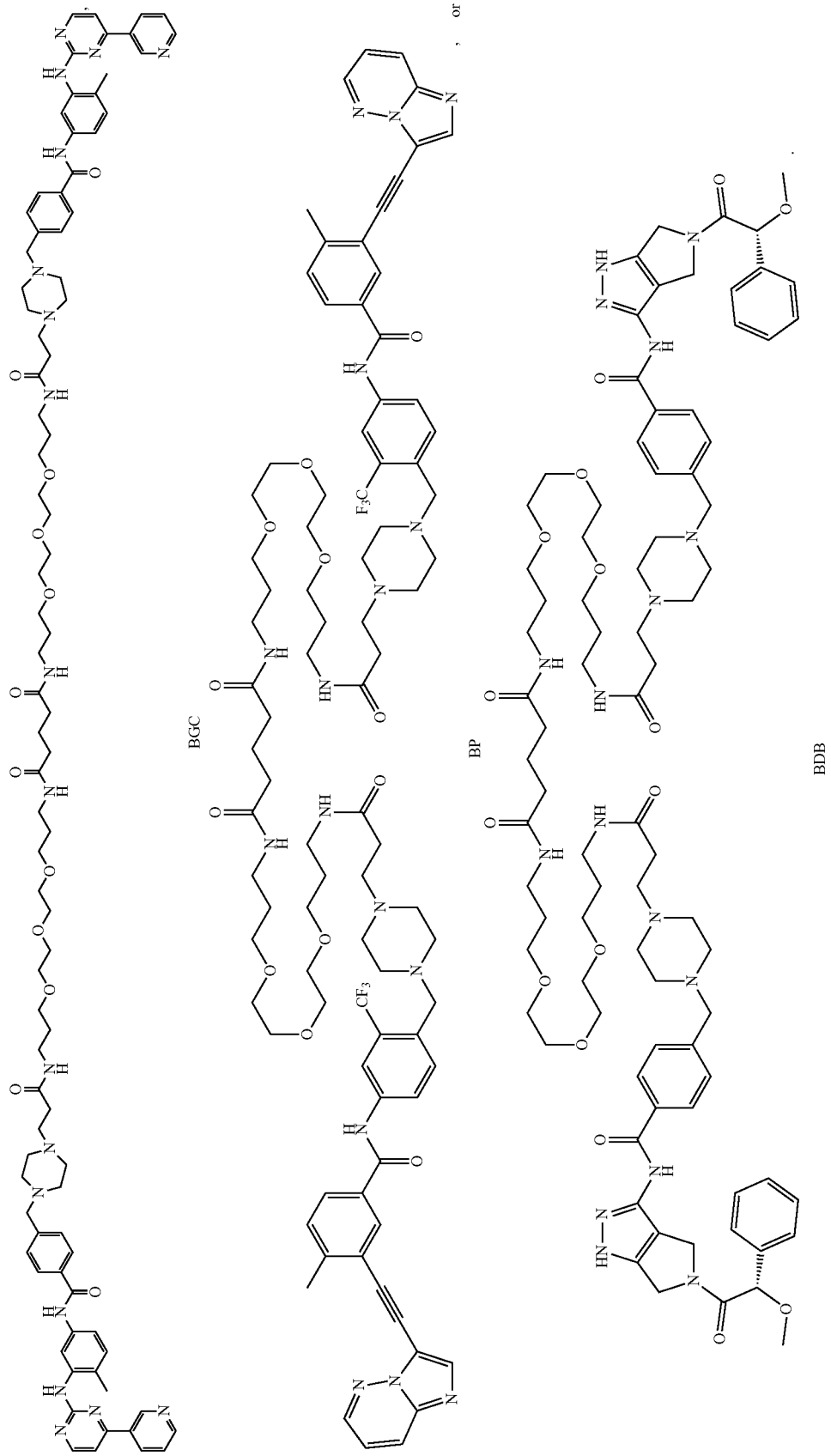

5. A method for synthesizing the compound of formula I, comprising:
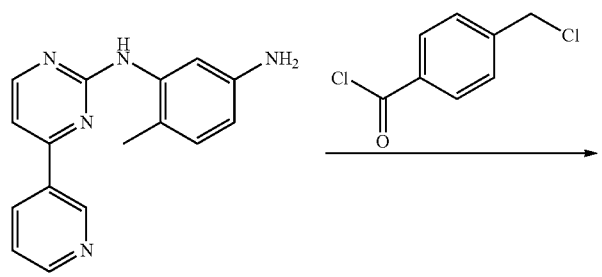
Compound 1a
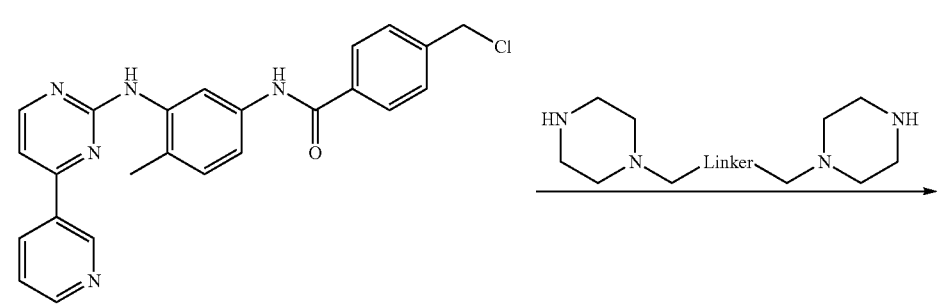
Compound 2a
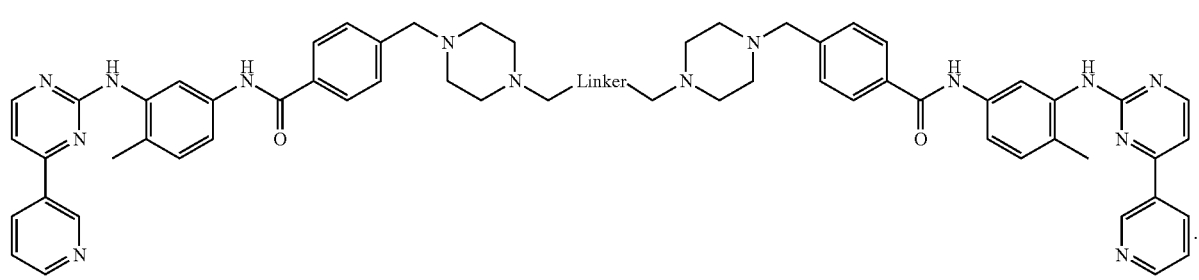
Compound I
6. The method for synthesizing the compound of formula I according to claim 5, comprising:
(1) synthesizing compound 2a:
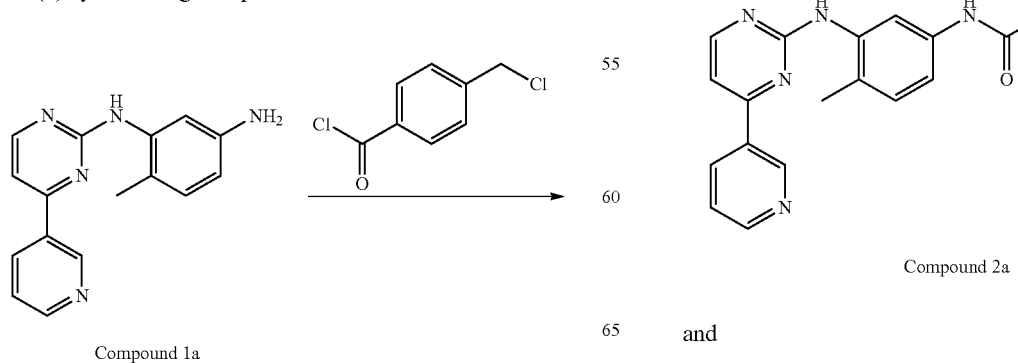
Compound 1a
Compound 2a
and
(2) synthesizing compound BGC:

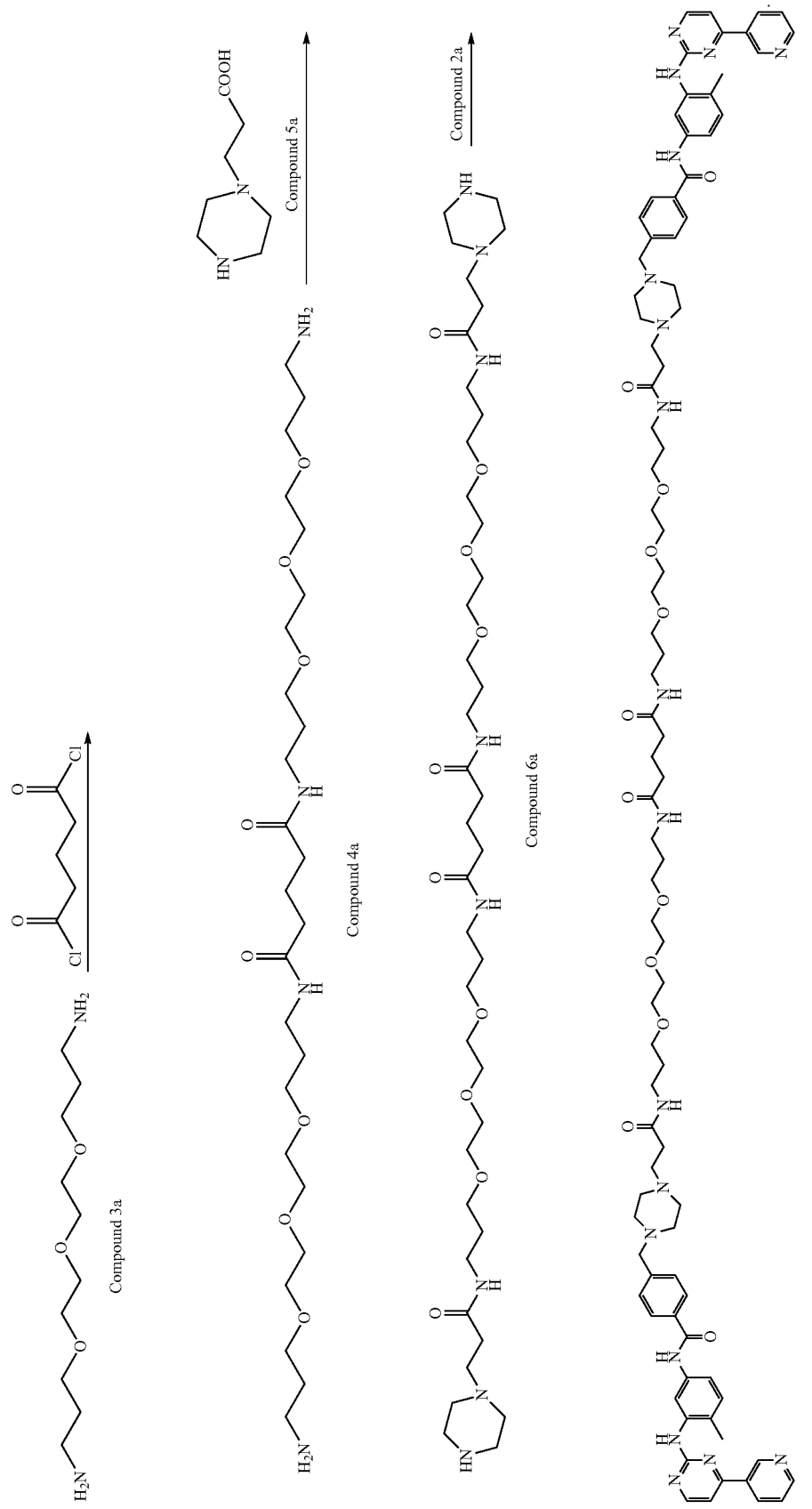

7. The method for synthesizing the compound of formula I according to claim 6, comprising:
   (a) synthesizing compound 2a, comprising: mixing compound 1a, triethylamine, and 4-(chloromethyl) benzoyl chloride in dichloromethane a first mixture, stirring the first mixture at room temperature for 18 hours, separating a first solid from the first mixture, and purifying the first solid to obtain compound 2a;
   (b) synthesizing of compound 6a, comprising:
      (1) mixing compound 3a, triethylamine, and glutaryl dichloride in dichloromethane to form a second mixture, stirring the second mixture at room temperature for 6 hours, separating a second solid from the second mixture, purifying the second solid to obtain compound 4a; and
      (2) mixing compound 4a, 1-hydroxy benzotrizole, 1-(3-dimethylaminopropyl)-3-ethylcarbodiimide hydrochloride and N-methylmorpholine in dichloromethane to for a third mixture, stirring the third mixture in an ice bath for 0.5 hours, then adding compound 5a into the third mixture to form a fourth mixture, reacting the fourth mixture at room temperature, separating a third solid from the fourth mixture; and purifying the third solid to obtain compound 6a; and
   (c) synthesizing of compound BGC, comprising: mixing compound 2a, compound 6a, and potassium carbonate in N,N-dimethyl formamide to form a third mixture, stirring the third mixture at 100° C. for 18 hours, separating a third solid from the third mixture, and purifying the third solid to obtain compound BGC.

8. The method for synthesizing the compound of formula I according to claim 7, wherein,
   in step (a), a molar ratio of compound 1a, triethylamine, and 4-(chloromethyl) benzoyl chloride is 18:35.6:21.3, a molar volume ratio of compound 1a and dichloromethane is 18: 400 mmol/ml;
   in sub-step (1) of step (b), a molar ratio of compound 3a, triethylamine, and glutaryl dichloride is 45.4: 68.1: 22.7, a molar volume ratio of compound 3a and dichloromethane is 45.4: 300 mmol/ ml;
   in sub-step (2) of step (b), a molar ratio of compound 4a, 1-hydroxy benzotrizole, 1-(3-dimethylaminopropyl)-3-ethylcarbodiimide hydrochloride, N-methylmorpholine, and compound 5a is 1: 1.2: 1.2: 3: 2.1, a molar volume ratio of compound 4a and dichloromethane is 1: 20 mmol/ ml; and
   in step (c), a molar ratio of compound 2a, compound 6a, and potassium carbonate is 0.28: 0.09: 2.69, a molar volume ratio of compound 2a and N,N-dimethyl formamide is 0.28: 20 mmol/ ml.

9. A method for synthesizing compound BP, comprising: synthesizing compound 12

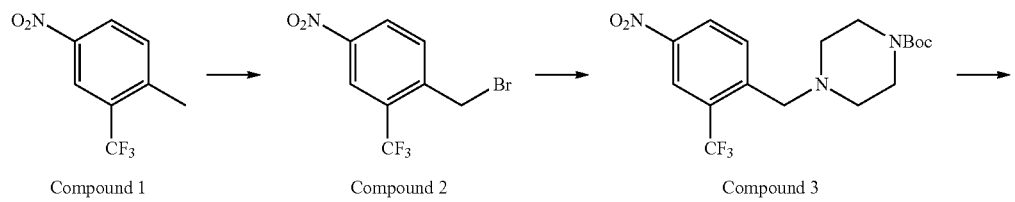

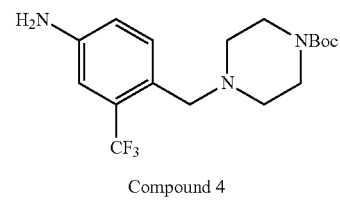

Compound 4

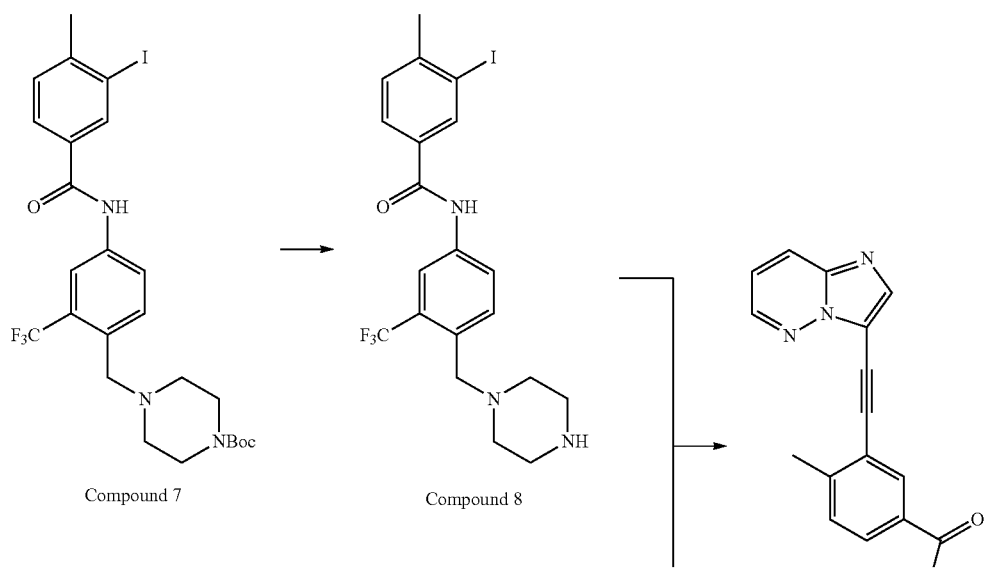

-continued
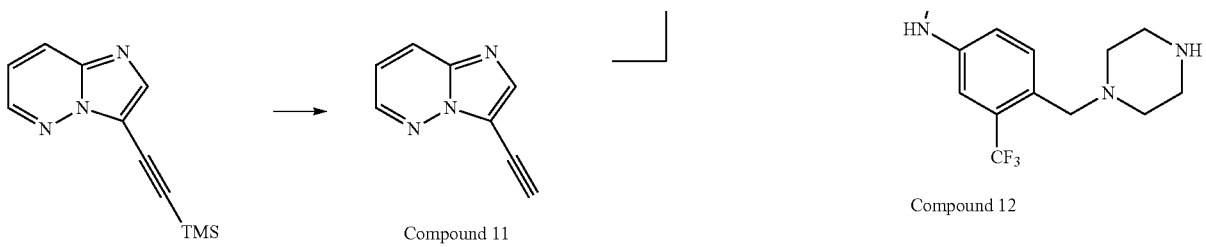
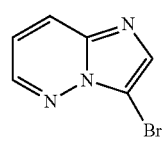
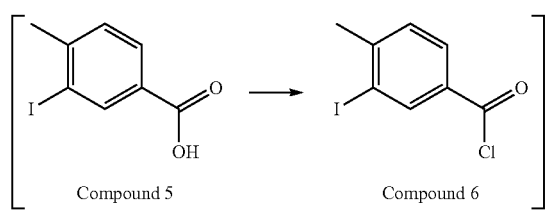
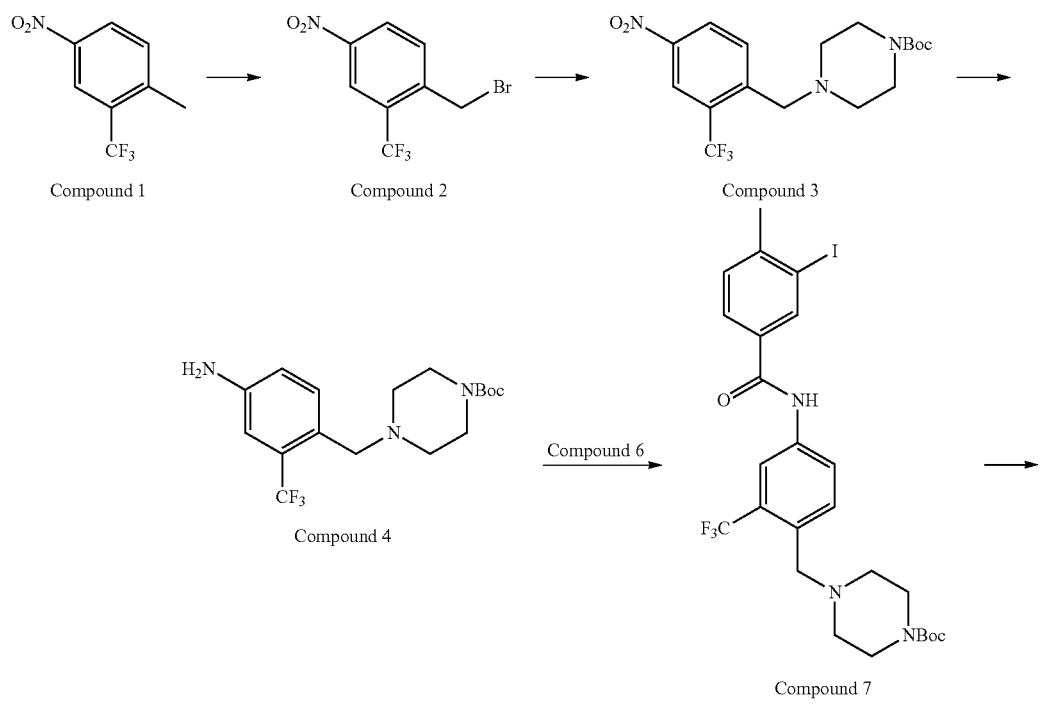

-continued
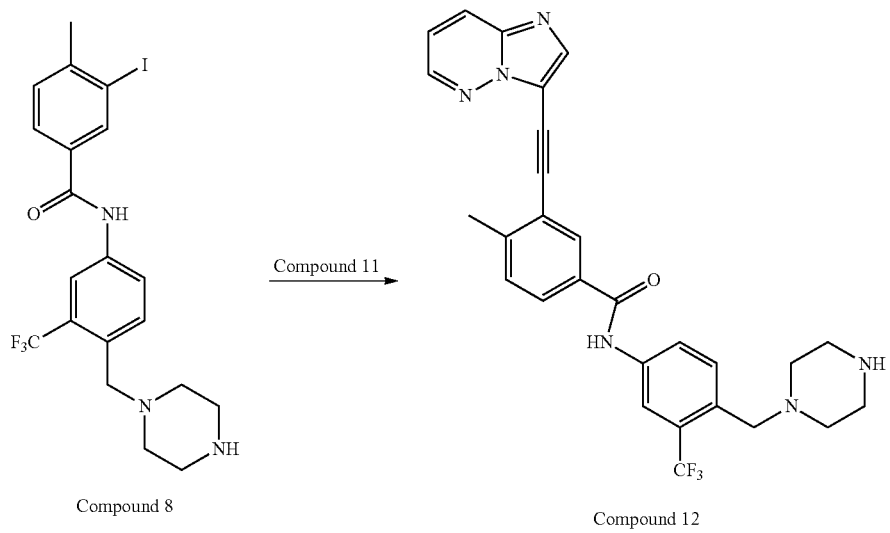
Compound 8 → Compound 12 (via Compound 11)
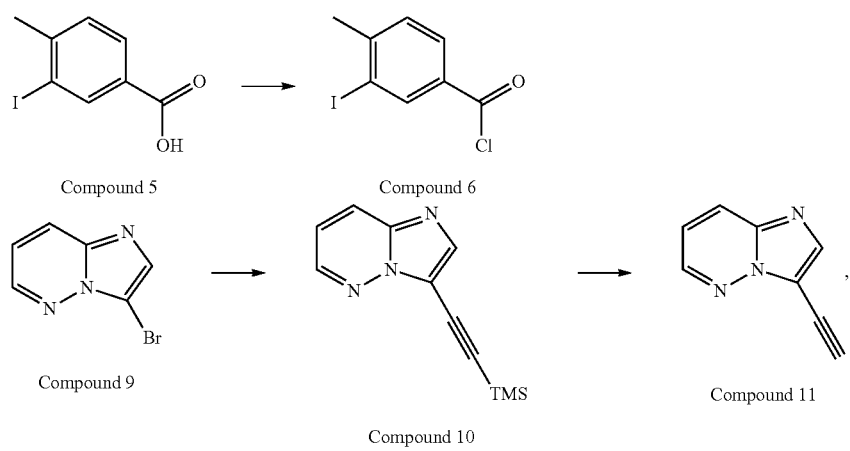
and compound BP
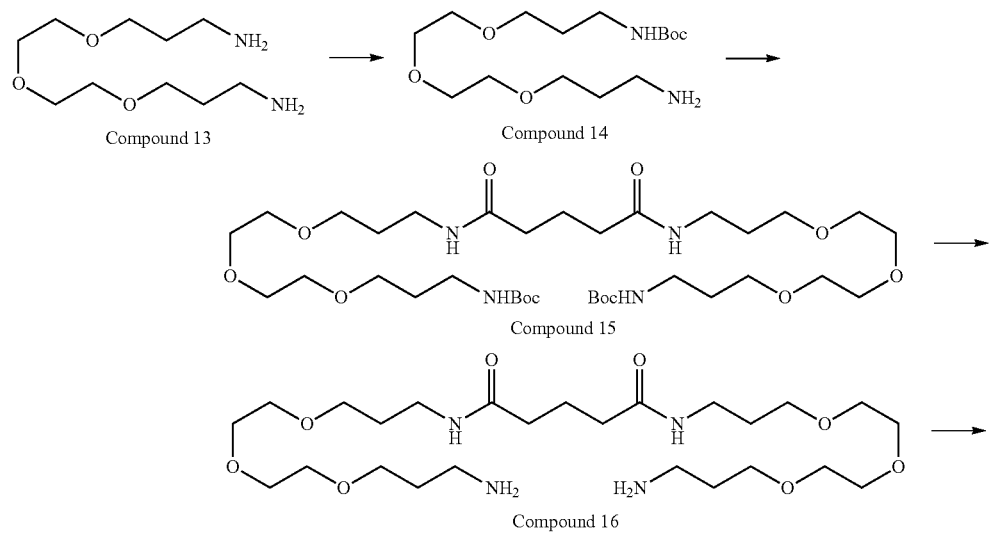

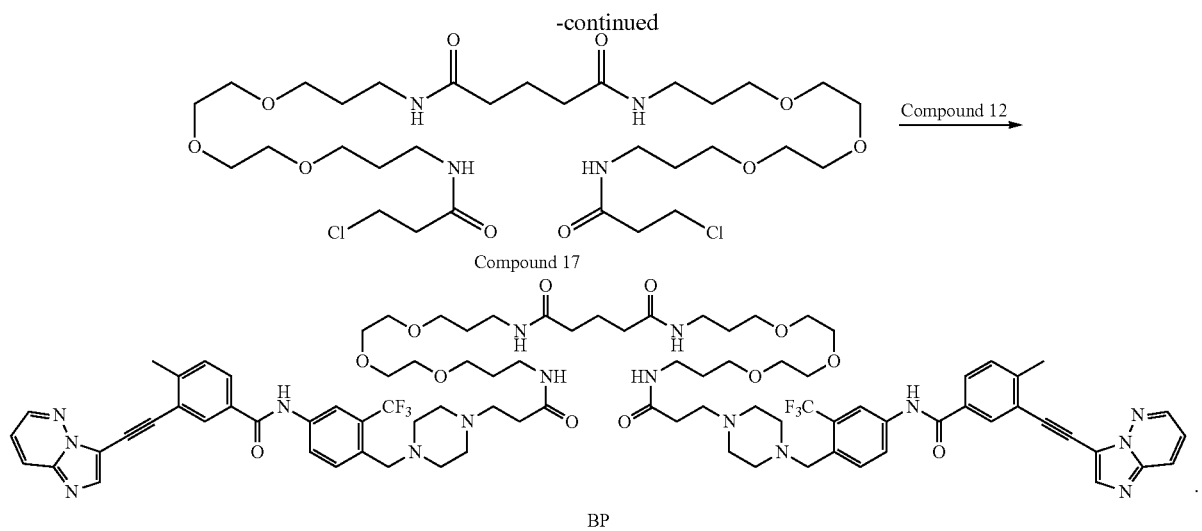

10. The method for synthesizing compound BP according to claim 9, comprising:
   i. synthesizing compound 4, comprising:
   (1) adding 2-methyl-5-nitrobenzotrifluoride (compound 1) into carbontetrachloride, further adding N-bromosuccinimide and 2,2'-azoisobutyronitrile under nitrogen protection to form a first solution, refluxing the first solution for 24 hours, then separating compound 2 from the first solution;
   (2) adding compound 2, N-boc-piperazine, and triethylamine into dichloromethane to form a second solution, stirring the second solution at room temperature for 3 hours, then separating a compound 3 from the second solution;
   (3) reducing iron powder, ammonium chloride, and compound 3 in a third solution containing water and ethanol, refluxing the third solution for 1 hours, then separating compound 4 from the third solution;
   ii. synthesizing compound 8, comprising:
   (4) adding 3-iodo-4-methylbenzoic acid and thionyl chloride into a fourth solution containing tetrahydrofuran and N,N-dimethylformamide, reacting at 60° C. for 1 hours, then separating compound 6 from the fourth solution;
   (5) adding compound 4, triethylamine and compound 6 in dichloromethane to form a fifth solution, reacting at room temperature, then separating compound 7 from the fifth solution;
   (6) adding compound 7 and HCl into methanol to form a sixth solution, reacting completely, separating compound 8 from the sixth solution;
   iii. synthesizing compound 11, comprising:
   (7) adding 3-bromoimidazo[1,2-b]pyridazine in acetonitrile, under protection of nitrogen, adding trans-dichlorobis(triphenylphosphine)palladium(II), cuprous iodide, dicyclohexylamine, and trimethylsilyl acetylene to form a seventh solution, reacting completely at 80° C., then separating compound 10 from the seventh solution;
   (8) mixing compound 10, methanol, and a saturated solution of potassium fluoride to form an eighth solution, reacting completely at room temperature, then separating compound 11 from the eighth solution;
   iv. synthesizing compound 12, comprising:
   (9) adding compound 8, compound 11 into N,N-dimethyl formamide, further adding trans-dichlorobis(triphenylphosphine)palladium(II), cuprous iodide, and N,N-diisopropylethylamine under nitrogen protection to form a ninth solution, reacting completely at room temperature, then separating compound 12 from the ninth solution;
   v. synthesizing compound 17, comprising:
   (10) adding compound 13, ditertbutyl pyrocarbonate into dichloromethane to form a tenth solution, reacting completely, then separating a compound 14 from the tenth solution;
   (11) adding compound 14, triethylamine, and glutaryl dichloride into dichloromethane to form an eleventh solution, stirring the eleventh solution for 3 hours, then separating compound 15 from the eleventh solution;
   (12) adding compound 15 into HCl/ethylacetate to form a twelfth solution, stirring the twelfth solution at room temperature for 3 hours, separating compound 16 from the twelfth solution;
   (13) adding compound 16, N,N-diisopropylethylamine, and 3-chloropropionyl chloride into dichloromethane to form a thirteenth solution, stirring thirteenth solution at room temperature for 3 hours, separating compound 17 from the thirteenth solution;
   vi. synthesizing compound BP, comprising:
   (14) adding compound 12, compound 17 and triethylamine into tetrahydrofuran to form a fifteenth solution, refluxing the fifteenth solution for 24 hours, then separating compound BP from the fifteenth solution.

11. The method for synthesizing compound BP according to claim 10, wherein,
   in sub-step (1) of step i, a molar ratio of 2-methyl-5-nitrobenzotrifluoride, N-bromosuccinimide, and 2,2'-azoisobutyronitrile is 0.15: 0.16: 0.01, a molar volume ratio of 2-methyl-5-nitrobenzotrifluoride and carbontetrachloride is 0.15: 200 mmol/ml;
   in sub-step (2) of step i, a molar ratio of compound 2, 1-boc-piperazine, and triethylamine is 0.146: 0.16: 0.22, a molar volume ratio of compound 2 and dichloromethane is 14.6: 200 mmol/ ml;
   in sub-step (3) of step i, a molar ratio of reduced iron powder, ammonium chloride and compound 3 is 0.5:

0.3: 0.1, a molar volume ratio of compound 3 and the third solution is 0.1: 200 mmol/ ml, and the volume ratio of water and ethanol is 1: 1;

in sub-step (4) of step ii, a molar volume ratio of 3-iodo-4-methylbenzoic acid and the mixture is 0.09: 101mmol/ ml, a volume ratio of tetrahydrofuran and N,N-dimethylformamide is 100: 1;

in sub-step (5) of step ii, a molar ratio of compound 4, triethylamine and compound 6 is 0.08: 0.12: 0.088, a molar volume ratio of compound 4 and dichloromethane is 0.08:250 mmol/ ml;

in sub-step (6) of step ii, a molar volume ratio of compound 7 and methanol is 0.03: 100mmol/ ml;

in sub-step (7) of step iii, a molar volume ratio of 3-bromoimidazo[1,2-b]pyridazine and acetonitrile is 0.05: 100 mmol/ ml, a molar ratio of 3-bromoimidazo[1,2-b]pyridazine, trans-dichlorobis(triphenylphosphine)palladium(II), cuprous iodide, dicyclohexylamine, and trimethylsilyl acetylene is 0.05: 0.0014: 0.0014: 0.06: 0.6;

in sub-step (8) of step iii, a molar volume ratio of compound 10 and methanol is 0.04: 50mol/ml, a volume ratio of methanol and saturated solution of potassium fluoride is 50: 20;

in sub-step (9) of step iv, a molar ratio of compound 8, compound 11, trans-dichlorobis (triphenylphosphine) palladium(II), cuprous iodide and N,N-diisopropylethylamine is 17.3: 19: 1: 1: 38, a molar volume ratio of compound 8 and N,N-dimethylformamide is 17.3: 150mmol/ ml;

in sub-step (10) of step v, a molar ratio of compound 13 and ditertbutyl pyrocarbonate is 45.5: 43.18, a volume ratio of compound 13 and dichloromethane is 45.5: 600 mmol/ ml;

in sub-step (11) of step v, a molar ratio of compound 14, triethylamine and glytaryl dichloride is 8.42: 14.85: 4.17, a molar volume ratio of compound 14 and dichloromethane is 8.42: 120 mmol/ ml;

in sub-step (12) of step v, a molar volume ratio of compound 15 and HCl/ethyl acetate is 3.8: 100 mmol/ ml, wherein a concentration of HCl/ethyl acetate is 2M;

in sub-step (13) of step v, a molar ratio of compound 16, N,N-diisopropylethylamine and 3-chloropropionyl chloride is 0.90: 6.15: 1.81, a molar volume ratio of compound 16 and dichloromethane is 0.90: 50 mmol/ ml; and in sub-step (14) of step vi, a molar ratio of compound 12, compound 17, and triethylamine is 0.2: 0.1: 0.3, a molar volume ratio of compound 12 and tetrahydrofuran is 0.2: 10 mmol/ ml.

12. A method for treating chronic myelogenous leukemia comprising administering to a subject in need thereof a therapeutically effective amount of the compound or the pharmaceutically acceptable salt thereof of claim 1.

13. The method according to claim 12, wherein the therapeutically effective amount of the compound or the pharmaceutically acceptable salt thereof of claim 1 is a tyrosine kinase inhibitor.

14. The method according to claim 12, wherein the therapeutically effective amount of the compound or the pharmaceutically acceptable salt thereof of claim 1 is an ABL inhibitor.

15. The method according to claim 12, wherein the therapeutically effective amount of the compound or the pharmaceutically acceptable salt thereof of claim 1 is an inhibitor of BCR-ABL or a mutant thereof.

16. The method according to claim 15, wherein the BCR-ABL mutant is T315I.

\* \* \* \* \*